(12) United States Patent
Groothuis et al.

(10) Patent No.: US 8,226,709 B2
(45) Date of Patent: Jul. 24, 2012

(54) METHOD AND SYSTEM FOR PLICATING TISSUE IN A MINIMALLY INVASIVE MEDICAL PROCEDURE FOR THE TREATMENT OF MITRAL VALVE REGURGITATION

(75) Inventors: Adam Groothuis, Swampscott, MA (US); Matthew Krever, Warren, NJ (US); Timothy Lash, Hillsborough, NJ (US); Rudolph Cedro, Clinton, NJ (US); Ted Bachman, Easton, PA (US); Paul D'Antonio, Morristown, NJ (US); Erin Black, Middlesex, NJ (US); Daniel H. Olsen, Califon, NJ (US); Salvatore G. Caldarise, Belle Mead, NJ (US); Natalie D. Macon, Basking Ridge, NJ (US); Paritosh Dhawale, Martinsville, NJ (US)

(73) Assignee: Cordis Corporation

( * ) Notice: Subject to any disclaimer, the term of this patent is extended or adjusted under 35 U.S.C. 154(b) by 780 days.

(21) Appl. No.: 12/249,388

(22) Filed: Oct. 10, 2008

(65) Prior Publication Data
US 2009/0105814 A1   Apr. 23, 2009

Related U.S. Application Data

(60) Provisional application No. 60/981,303, filed on Oct. 19, 2007.

(51) Int. Cl.
*A61F 2/24* (2006.01)
*A61B 17/10* (2006.01)
(52) U.S. Cl. .................. 623/2.11; 606/139; 606/142
(58) Field of Classification Search .............. 623/2.1, 623/2.11; 606/139, 142, 213, 232; 128/898
See application file for complete search history.

(56) References Cited

U.S. PATENT DOCUMENTS

| | | | |
|---|---|---|---|
| 4,204,541 | A | 5/1980 | Kapitanov |
| 4,586,923 | A | 5/1986 | Gould et al. |
| 4,636,346 | A | 1/1987 | Gold et al. |
| 5,088,979 | A | 2/1992 | Filipi et al. |

(Continued)

FOREIGN PATENT DOCUMENTS

WO   WO 0060995   10/2000

(Continued)

OTHER PUBLICATIONS

Office Action mailed Jul. 21, 2011 in related U.S. Appl. No. 12/341,493.

(Continued)

*Primary Examiner* — Dianne Dornbusch

(57) ABSTRACT

A system and method for the treatment of mitral valve regurgitation by reshaping the mitral valve annulus using one or more plications of annular or adjacent tissue each fixed by a retainer is described. The system includes four devices to achieve such percutaneous direct plication annuloplasty. The first is a crossing catheter having a prolapseable or curved tip. Second, a deflecting guide catheter is used to provide a means for guiding the plication device into proper position at the subvalvular region of the mitral valve annulus. Third, the plication device is then used to make plications in the subvalvular region of the mitral valve annulus. Fourth, a "C" shaped retainer with deformable ends is deployed by the plication device in order to retain the plicated tissue in the plicated form. A transseptal approach may be used to plicate and retain tissue on the atrial side of the mitral valve to achieve a reduction in mitral valve regurgitation.

43 Claims, 17 Drawing Sheets

U.S. PATENT DOCUMENTS

| | | | |
|---|---|---|---|
| 5,099,827 | A | 3/1992 | Melzer et al. |
| 5,403,326 | A | 4/1995 | Harrison et al. |
| 5,437,266 | A | 8/1995 | McPherson et al. |
| 5,487,757 | A | 1/1996 | Truckai et al. |
| 5,545,148 | A | 8/1996 | Wurster |
| 5,582,616 | A | 12/1996 | Bolduc et al. |
| 5,716,367 | A * | 2/1998 | Koike et al. ............... 606/144 |
| 5,738,631 | A | 4/1998 | Konstorum |
| 5,830,221 | A | 11/1998 | Stein et al. |
| 5,865,791 | A | 2/1999 | Whayne et al. |
| 5,968,010 | A * | 10/1999 | Waxman et al. ............ 600/500 |
| 5,997,556 | A | 12/1999 | Tanner |
| 6,015,416 | A | 1/2000 | Stefanchik et al. |
| 6,086,600 | A | 7/2000 | Kortenbach |
| 6,113,611 | A | 9/2000 | Allen et al. |
| 6,152,935 | A | 11/2000 | Kammerer et al. |
| 6,165,164 | A | 12/2000 | Hill et al. |
| 6,267,781 | B1 | 7/2001 | Tu |
| 6,269,819 | B1 | 8/2001 | Oz et al. |
| 6,352,503 | B1 | 3/2002 | Matsui et al. |
| 6,482,224 | B1 * | 11/2002 | Michler et al. ............. 606/219 |
| 6,494,888 | B1 | 12/2002 | Laufer et al. |
| 6,520,973 | B1 | 2/2003 | McGarry |
| 6,619,291 | B2 * | 9/2003 | Hlavka et al. ............. 128/898 |
| 6,626,917 | B1 | 9/2003 | Craig |
| 6,629,534 | B1 | 10/2003 | St. Goar et al. |
| 6,718,985 | B2 | 4/2004 | Hlvaka et al. |
| 6,736,828 | B1 | 5/2004 | Adams et al. |
| 6,740,098 | B2 | 5/2004 | Abrams et al. |
| 6,921,361 | B2 | 7/2005 | Suzuki et al. |
| 6,945,978 | B1 | 9/2005 | Hyde |
| 7,011,669 | B2 | 3/2006 | Kimblad |
| 7,029,468 | B2 | 4/2006 | Honebrink |
| 7,037,334 | B1 * | 5/2006 | Hlavka et al. ............. 623/2.36 |
| 7,166,127 | B2 | 1/2007 | Spence et al. |
| 7,226,467 | B2 * | 6/2007 | Lucatero et al. ............. 606/213 |
| 7,306,614 | B2 | 12/2007 | Weller et al. |
| 7,404,824 | B1 | 7/2008 | Webler et al. |
| 7,666,204 | B2 * | 2/2010 | Thornton et al. ............. 606/190 |
| 7,727,246 | B2 | 6/2010 | Sixto, Jr. et al. |
| 7,799,038 | B2 * | 9/2010 | Sogard et al. ............. 606/139 |
| 7,799,040 | B2 | 9/2010 | Stokes et al. |
| 7,860,555 | B2 | 12/2010 | Saadat |
| 7,914,542 | B2 | 3/2011 | Lamson et al. |
| 2001/0005787 | A1 | 6/2001 | Oz et al. |
| 2002/0087169 | A1 * | 7/2002 | Brock et al. ............. 606/139 |
| 2002/0103492 | A1 | 8/2002 | Kaplan et al. |
| 2002/0111637 | A1 * | 8/2002 | Kaplan et al. ............. 606/139 |
| 2003/0055442 | A1 | 3/2003 | Laufer et al. |
| 2003/0065340 | A1 | 4/2003 | Geitz |
| 2003/0065359 | A1 | 4/2003 | Weller et al. |
| 2003/0100943 | A1 | 5/2003 | Bolduc |
| 2003/0120264 | A1 | 6/2003 | Lattouf |
| 2003/0130561 | A1 | 7/2003 | Suzuki et al. |
| 2003/0130571 | A1 * | 7/2003 | Lattouf ........................ 600/374 |
| 2003/0167071 | A1 | 9/2003 | Martin et al. |
| 2003/0208211 | A1 | 11/2003 | Kortenbach |
| 2004/0010245 | A1 | 1/2004 | Cerier et al. |
| 2004/0019378 | A1 * | 1/2004 | Hlavka et al. ............. 623/2.11 |
| 2004/0044364 | A1 | 3/2004 | DeVries et al. |
| 2004/0092962 | A1 * | 5/2004 | Thornton et al. ............. 606/139 |
| 2004/0127919 | A1 | 7/2004 | Trout et al. |
| 2004/0138682 | A1 | 7/2004 | Onuki et al. |
| 2004/0147958 | A1 | 7/2004 | Lam et al. |
| 2004/0186566 | A1 | 9/2004 | Hindrichs et al. |
| 2004/0193193 | A1 | 9/2004 | Laufer et al. |
| 2005/0075654 | A1 | 4/2005 | Kelleher |
| 2005/0119524 | A1 | 6/2005 | Sekine et al. |
| 2005/0149014 | A1 | 7/2005 | Hauck et al. |
| 2005/0192629 | A1 | 9/2005 | Saadat et al. |
| 2005/0216036 | A1 | 9/2005 | Nakao |
| 2005/0234512 | A1 | 10/2005 | Nakao |
| 2005/0251162 | A1 | 11/2005 | Rothe et al. |
| 2005/0251166 | A1 | 11/2005 | Vaughan et al. |
| 2005/0251202 | A1 | 11/2005 | Ewers et al. |
| 2005/0272977 | A1 | 12/2005 | Saadat et al. |
| 2005/0277945 | A1 | 12/2005 | Saadat et al. |
| 2005/0277954 | A1 | 12/2005 | Smith et al. |
| 2006/0030885 | A1 | 2/2006 | Hyde |
| 2007/0010857 | A1 * | 1/2007 | Sugimoto et al. ............. 606/232 |
| 2007/0025737 | A1 | 2/2007 | Kamio et al. |
| 2007/0032797 | A1 | 2/2007 | Ortiz et al. |
| 2007/0055335 | A1 | 3/2007 | Feldmann et al. |
| 2007/0118151 | A1 * | 5/2007 | Davidson ........................ 606/144 |
| 2007/0118155 | A1 | 5/2007 | Goldfarb et al. |
| 2007/0142849 | A1 | 6/2007 | Ewers et al. |
| 2007/0265610 | A1 | 11/2007 | Thapliyal et al. |
| 2007/0265702 | A1 * | 11/2007 | Lattouf ........................ 623/2.12 |
| 2008/0033241 | A1 * | 2/2008 | Peh et al. ........................ 600/109 |
| 2008/0228266 | A1 * | 9/2008 | McNamara et al. ......... 623/2.36 |
| 2008/0228267 | A1 * | 9/2008 | Spence et al. ............. 623/2.36 |
| 2009/0024143 | A1 | 1/2009 | Crews et al. |
| 2009/0275964 | A1 | 11/2009 | Zeiner et al. |

FOREIGN PATENT DOCUMENTS

| | | |
|---|---|---|
| WO | WO 00/78227 | 12/2000 |
| WO | WO 2005/009286 | 2/2005 |

OTHER PUBLICATIONS

Office Action mailed Nov. 25, 2011 in related U.S. Appl. No. 12/249,675.

Office Action mailed Nov. 28, 2011 in related U.S. Appl. No. 12/249,551.

International Search Report mailed Sep. 15, 2010 from corresponding International Application No. PCT/US2009/068911.

* cited by examiner

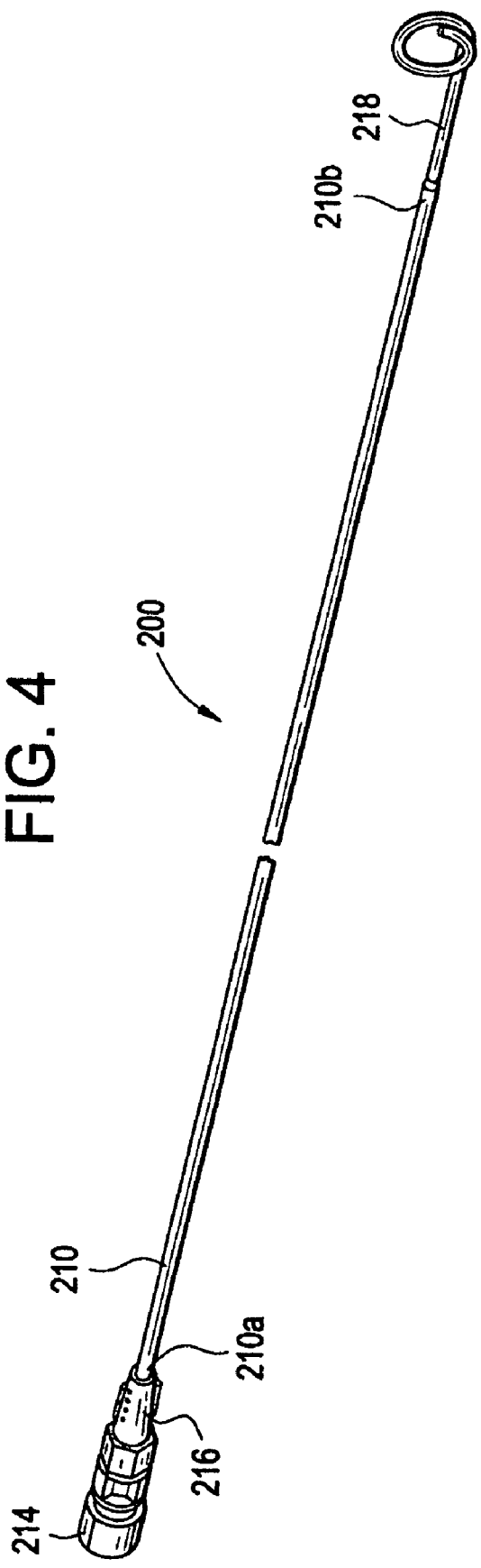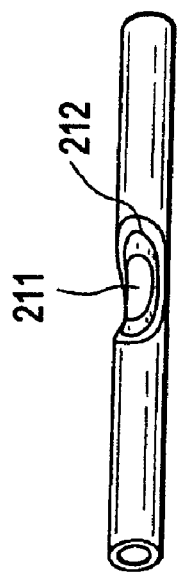
FIG. 4
FIG. 5

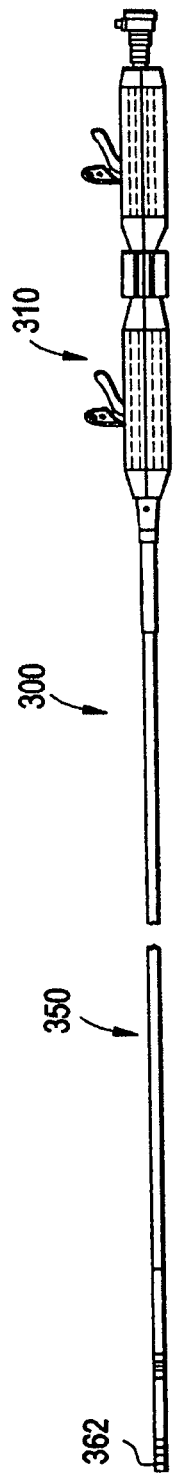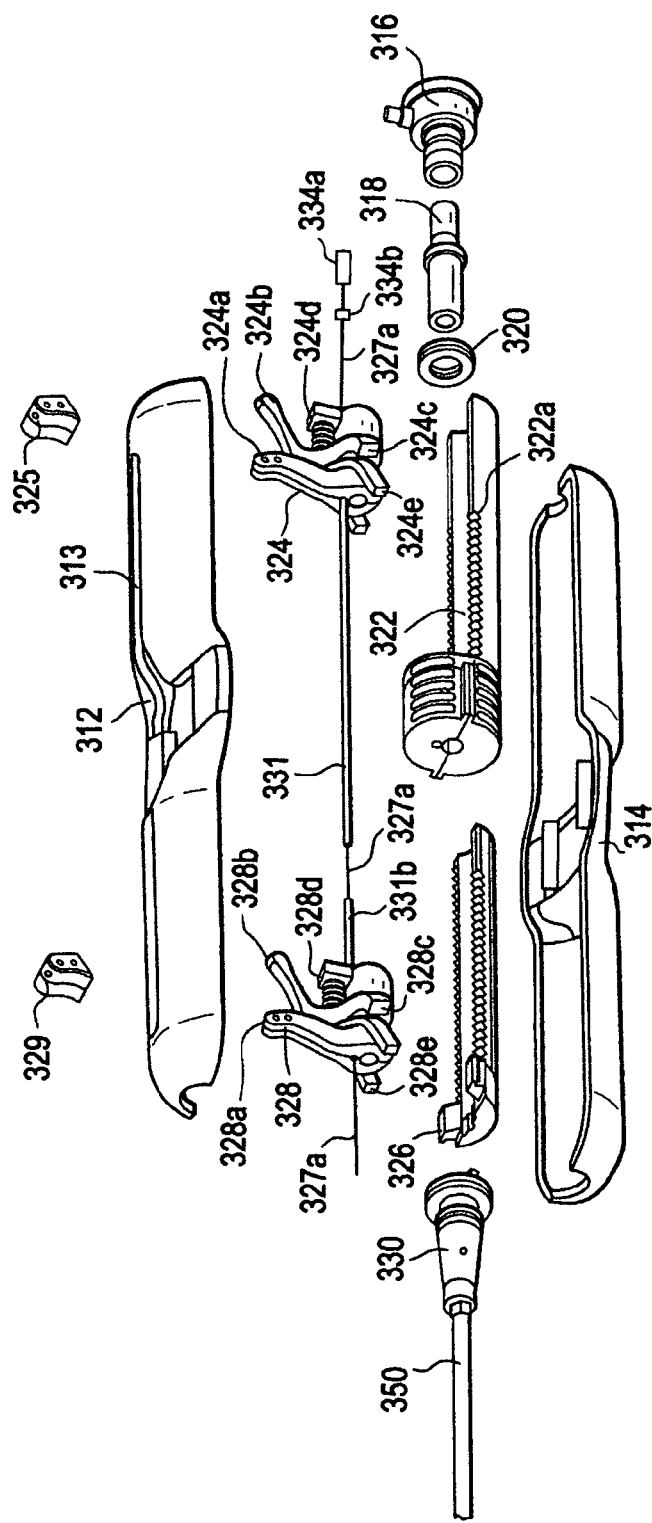

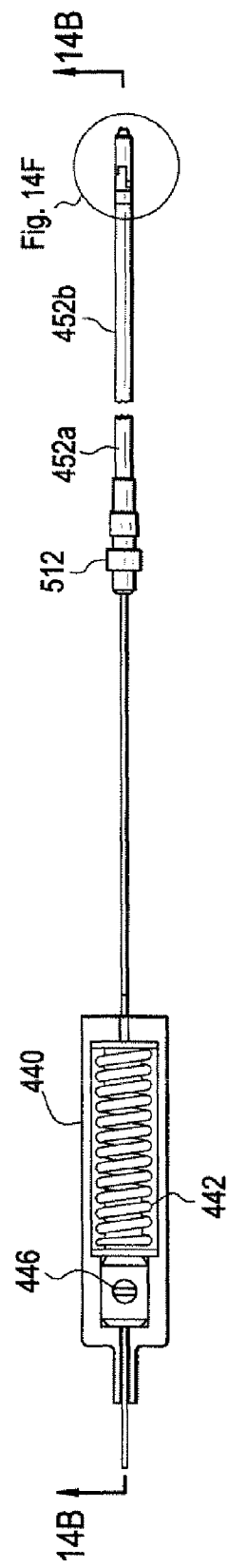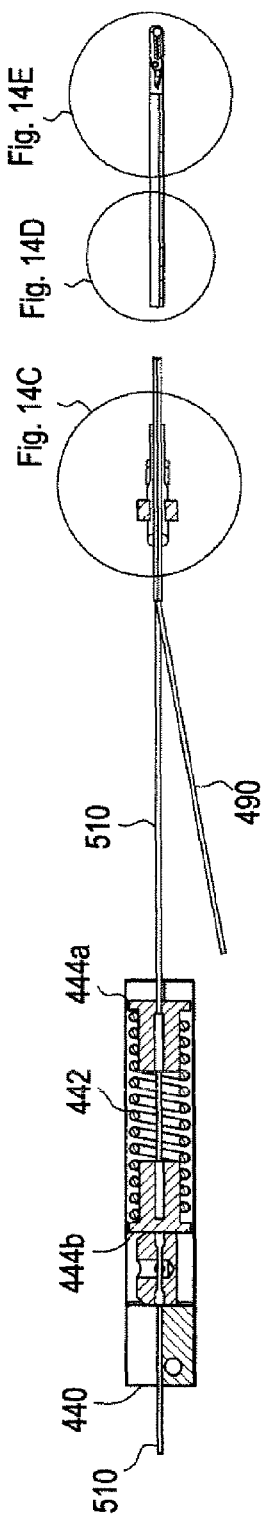

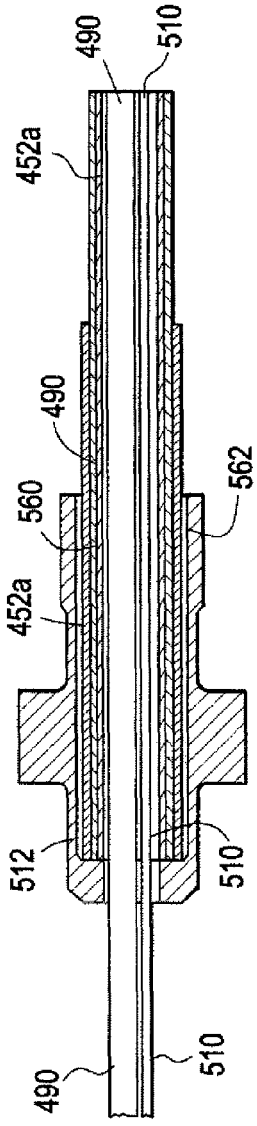
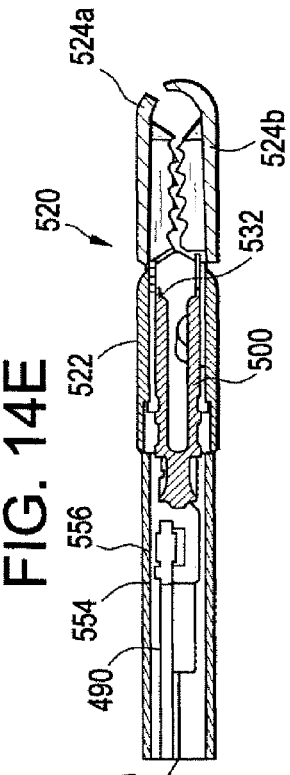
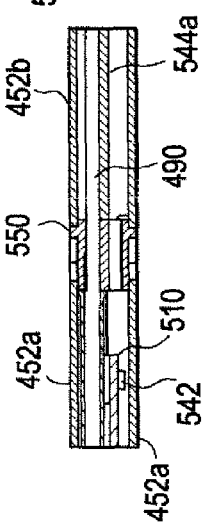
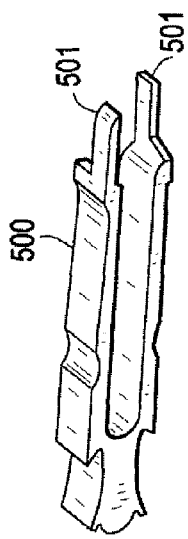
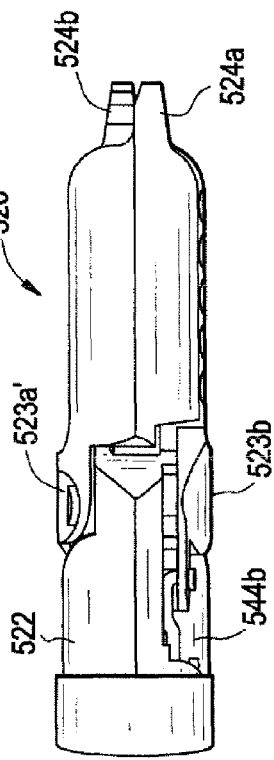
FIG. 14C
FIG. 14D
FIG. 14E
FIG. 14F
FIG. 15

METHOD AND SYSTEM FOR PLICATING TISSUE IN A MINIMALLY INVASIVE MEDICAL PROCEDURE FOR THE TREATMENT OF MITRAL VALVE REGURGITATION

CROSS-REFERENCE TO RELATED APPLICATIONS

This application claims the benefit of U.S. Provisional Patent Application No. 60/981,303 filed Oct. 19, 2007 which is hereby incorporated by reference in its entirety.

FIELD OF THE INVENTION

The present invention relates to a device and method for treating the vasculature and internal organs of a patient. Particularly, the present invention is directed to a system and method for treating mitral valve regurgitation in the heart of a patient using direct plication annuloplasty.

BACKGROUND OF THE INVENTION

Catheter based devices are used to treat a wide variety of medical problems in a minimally invasive manner. Catheters are used to place and expand angioplasty balloons used to widen veins and arteries narrowed by plaque. Small scaffolds called stents have been introduced into the vasculature using catheter-based systems in order to prevent the restenosis of such vessels. One of the problems that a catheter based device and system could be used to treat in a minimally invasive manner is mitral valve regurgitation, however, no commercially successful device for the treatment of mitral valve regurgitation in such a manner currently exists.

Mitral valve regurgitation is the backflow of blood from the left ventricle into the left atrium due to an improper alignment of the leaflets of the mitral valve thereby causing an imperfect closure of the valve. A gap between the anterior leaflet and posterior leaflet of the mitral valve is created by the improper closure providing a conduit for blood to flow through the mitral valve in a retrograde manner from the left ventricle to the left atrium. This gap may be a congenital defect or may be caused by disease, i.e., ischemic or idiopathic cardiomyopathy and/or intrinsic degenerative disease of components of the mitral valve apparatus. One type of condition, congestive heart failure (CHF), causes the heart to enlarge. In an enlarged heart the walls of the left ventricle are expanded or dilated which causes the papillary muscles to be displaced downward and/or outward resulting in a tethering of the chordae tendineae and subsequent tethering/pulling on the leaflets. Also, with CHF, the mitral annulus is dilated. The combination of the dilated annulus and the tethering on the leaflets prevents the leaflets from closing properly, thereby causing the problematic gap in the mitral valve. The resultant backflow through the mitral valve reduces the efficiency of the heart resulting in a need for the heart to beat faster and/or more forcefully in order to produce the same amount of blood flow. Mitral valve regurgitation may be asymptomatic in some patients but in other patients the reduction in blood flow and the resultant strain on the heart could result in arrhythmias, heart attack and possibly death.

The preferred current treatments for mitral valve regurgitation require open-heart surgery and/or the use of endoscopic techniques that are difficult for the surgeon and potentially dangerous for the patient. In one method of treatment, porcine heart valves or mechanical heart valves are used to replace the damaged or defective mitral valve. Such treatments require the use of open-heart surgery to accomplish the implantation. Such heterologous valves may be used in humans but often wear-out prematurely and additional open-heart surgery is required to replace such valves with additional heterologous or mechanical valves. Mechanical valves have been developed which may also be used as a replacement for a defective mitral valve, however, the implantation of a mechanical valve usually indicates long-term anti-coagulant therapy to prevent clots from developing around the valve that could lead to a dangerous embolism. Long-term anticoagulant treatment causes other problems such as unwanted internal and external bleeding and possibly strokes.

Another open-heart surgical procedure for treating functional mitral valve regurgitation is annuloplasty. In an annuloplasty procedure, a generally "D" shaped annuloplasty ring is implanted on the mitral valve annulus to reduce the size of the stretched mitral valve annulus, most importantly, the septal-lateral dimension and improve closing (or coaptation) of the valve thereby reducing regurgitation. The surgeon surgically attaches, i.e., sews, the annuloplasty ring to the mitral valve on the atrial side of the mitral valve. The annuloplasty ring is sewn to the annulus on a top portion (i.e., the atrial side) of the mitral valve. Once implanted, tissue generally grows over the annuloplasty ring, and a line of contact between the annuloplasty ring and the mitral valve will essentially enable the mitral valve to appear and function as a normal mitral valve by reestablishing coaptation of the mitral valve leaflets but the durability of the effect is variable and may decline within six months after the procedure. Although a patient who receives the annuloplasty ring may be subjected to anti-coagulant therapies, the therapies are not extensive, as a patient is only subjected to the therapies for a matter of weeks, e.g., until tissue grows over the annuloplasty ring.

A second open-heart surgical procedure used in the treatment of degenerative mitral valve regurgitation is the Alfieri stitch procedure which the uses an edge-to-edge suture in the mitral valve. An edge-to-edge stitch is used to stitch together an area at approximately the center of a gap defined between the anterior and posterior leaflets of the mitral valve. Once the stitch is in place, the stitch is pulled in to form a suture that holds the anterior leaflet against the posterior leaflet. By reducing the size of the gap between the anterior leaflet and the posterior leaflet, the amount of leakage through the mitral valve may be substantially reduced. Durability has been a concern for Alfieri procedures done without the addition of an annuloplasty ring. In addition, use of the edge-to-edge procedure is only indicated in certain degenerative pathologies where the primary abnormality or gap between the leaflets is centrally located.

Another method of treating mitral valve regurgitation is the implantation of a ventricular assist device. Such devices are expensive and difficult to implant and require the patient to use anti-coagulant therapy indefinitely. Long-term use of anti-coagulant therapy may result in unnecessary bleeding and strokes. Such ventricular assist devices are, therefore, indicated for use only in patients that would likely not survive without their use and are used to keep patients alive who are candidates for heart transplant surgery. Left ventricular assist devices are a "bridge" therapy rather than a final therapy.

While such invasive surgical procedures have under certain circumstances been shown to be effective in the treatment of mitral valve leakage, invasive surgical procedures often have significant drawbacks. Any time a patient undergoes open-heart surgery, there is a risk of infection. Opening the sternum and using a cardiopulmonary bypass machine has also been shown to result in a significant incidence of both short and long term neurological deficits.

Some minimally invasive procedures have been developed to treat mitral valve regurgitation but, to date, none have become commercially successful standard procedures. U.S. Pat. No. 6,619,291 to Hvlaka et al. discloses a minimally invasive method of performing annuloplasty including inserting an implant into a left ventricle and orienting the implant in the left ventricle substantially below the mitral valve. The implant and tissue around the mitral valve are connected and tension is provided to the implant in order to substantially reduce an arc length associated with the mitral valve.

In U.S. Pat. Nos. 6,718,985 and 7,037,334 to Hvalaka et al. a series of plications near the mitral valve are created by T-bars that are threaded together to reshape the mitral valve. In U.S. Pat. No. 7,166,127 a catheter based system for treatment of mitral valve regurgitation uses a retainers adapted to be secured to the annulus of the mitral valve with flexible tensile members coupled to the retainers. A crimping device deployable through the catheter compresses a crimp onto the flexible tensile members after they are pulled toward one another to reduce the circumferential length of the annulus. In this system the number of permanent implants required in order to achieve an initial effect, and commitment to these implants before success of effect is able to be determined are serious drawbacks.

In United States Patent Application Publication No. 2007/0093857, Rogers et al. describes a device and method for the treatment of mitral valve regurgitation using a minimally invasive procedure in which plications are made proximate the mitral valve of the patient and a retainer is placed to hold the plication.

United States Patent Application No. 2007/0032797 discloses a device for reducing the size of the stomach having a corkscrew-shaped anchor for placement in the gastric wall.

United States Patent Application No. 2007/0025737 to Messerly et al. discloses a surgical retainer having a generally helical shape and a device having jaws for grasping tissue into which the helical retainer may be driven.

United States Patent Application No. 2007/0055335 discloses an electrode probe having a corkscrew-shaped distal tip for use in cardiology applications.

The need remains for a device and method for treating mitral valve regurgitation that can be used efficiently and effectively in a minimally invasive procedure and that provides the physician with the ability to know that the procedure has resulted in the desired effect prior to removing the device from the patient thereby reducing the need for and expense of repeat procedures. Such a procedure should provide the physician with the ability to changes the effect on the mitral valve during the procedure before taking an irreversible action.

SUMMARY OF THE INVENTION

The present invention provides a system and method for the treatment of mitral valve regurgitation. The method preferably uses a femoral retrograde approach of crossing the aortic valve. Access to the left ventricle is achieved through the aortic valve using the standard retrograde femoral artery approach utilizing a rounded crossing catheter (CC) preferably with a "J" or pigtail configuration. A deflecting guide catheter is then sent over the crossing catheter into the left ventricle. When the distal end of the deflectable catheter is in the left ventricle the crossing catheter is removed. The deflectable guide is preferably, but need not be, positioned between the papillary muscles with the distal segment lying along the posterior wall of the left ventricle and its tip is pointing towards the underside of the posterior mitral annulus. A plication device is then introduced through the deflectable catheter and is advanced out of the distal end of the deflectable catheter and is directed at the underside of the mitral valve, more preferably into the subvalvular groove and positioned so as to be able to grasp and plicate the tissue of the mitral valve at or near the annulus.

A test plication of the mitral valve annulus is created and the appropriateness of the plication is examined using imaging means such as TEE, ICE, TTE or fluoroscopy with or without contrast injection. If the plication is determined to be appropriate then a retainer is applied to the plication to retain the tissue in the plicated state. If the plication is not satisfactory then a retainer is not applied and the jaws of the plication device are released and the plicator is repositioned to plicate a different tissue target at or near the annulus of the mitral valve. Such "test" plications may be repeated a number of times prior to deploying the retainer.

If a single plication and retainer do not sufficiently reshape the mitral valve to correct the regurgitation then the original deflectable guide is repositioned and a second plicator with a retainer is introduced into the delivery guide and positioned and used in the same manner. Alternatively, a multi-retainer plicator can be used to provide the second or third retainers as necessary during the procedure without requiring the removal and reintroduction of the plication device. Once satisfactory changes in the annular geometry of the mitral valve and concomitant reduction in mitral valve regurgitation is achieved then the plication device and the deflectable guide are fully withdrawn and the femoral access site is closed using conventional closing techniques.

Four components comprise the system for percutaneous direct plication annuloplasty. The first is a prolapsable or curved tip crossing catheter preferably having a "J" or pigtail configuration. This may be used with or without a guidewire. In either case the crossing catheter is inserted in a stack or telescoped configuration with the second component, a deflecting guide catheter within which the crossing catheter is initially telescoped or stacked. The deflecting guide catheter is used to provide a means for guiding the plication device into proper position on the underside of the mitral valve preferably at the subvalvular region of the mitral valve at or near the annulus. The third component of the system is a plication device that has an end effector having opposing members at least one of which can be manipulated to open. The plication device is used to grasp tissue and also contains at least one retainer to retain the tissue in the plicated form if desired. The retainer in the preferred embodiment is a "C" shaped retainer having an end portion and two substantially perpendicular prongs that are pushed into the plicated tissue. The ends of the prongs may be compressed to increase the pressure on the plicated tissue and to prevent the retainer from being dislodged from the plicated tissue.

The present invention is a method for the percutaneous treatment of mitral valve regurgitation by reshaping a mitral valve annulus through an arterial access site in a patient comprising the steps of inserting a crossing catheter and a deflecting guide catheter having a lumen therethrough ending in a distal opening into the arterial access site of the patient; advancing the crossing catheter through the aortic valve into the left ventricle; advancing the deflecting guide catheter over the crossing catheter through the aortic valve into the left ventricle; withdrawing the crossing catheter from the patient; positioning the deflectable guide catheter with the distal opening pointing towards the underside of the mitral valve annulus; introducing a plication device into the arterial access site through the lumen of the deflectable guide catheter and advancing the plication device out the distal opening of the deflectable guide catheter; positioning the plication device at a first position in on the underside of the mitral valve at or near the annulus; plicating a first portion of tissue of the mitral valve using the plication device to create a first tissue plication; and applying a retainer to the first tissue plication.

Additionally the method can include the steps of examining the first tissue plication using an imaging method to produce an image of the mitral valve; and, determining if the plication is acceptable prior to the step of applying the retainer. Furthermore, the method can include the steps of: releasing the plication if the plication is determined not to be appropriate at the examining step; repositioning the plication device at a second position in the subvalvular groove of the mitral valve annulus; and plicating a first portion of tissue of the mitral valve at or near the annulus using the plication device to create a first tissue plication. The method may also include the steps of: determining if the first tissue plication as retained by the retainer sufficiently reshapes the mitral valve annulus to treat the mitral valve regurgitation; repositioning the deflectable guide catheter to a second position on the underside of the mitral valve at or near the annulus; introducing a second plication device or using a reloaded multi-retainer plication device in the delivery guide catheter and positioning the second plication device in the subvalvular region of the mitral valve; plicating a second portion of tissue of the mitral valve at or near the annulus using the plication device to create a second tissue plication; and; applying a retainer to the second tissue plication. Finally, the method may include the steps of withdrawing the deflectable guide catheter and the plication device and closing the arterial access site.

The present invention is directed to a system for the treatment of mitral valve regurgitation through direct plication annuloplasty of a patient that includes a deflecting guide catheter having an elongate body with lumen therethrough ending in a distal opening for insertion through the aortic valve into the left ventricle of the patient, a plication device having a set of opposing jaws operable to plicate tissue in the mitral valve of the patient, wherein the plication device comprises at least one retainer for retaining plications in tissue. Optionally, the system includes a crossing catheter having a distal end for insertion through the aortic valve into the left ventricle of the patient. The crossing catheter may be J-shaped or pigtail shaped. The system may also include a guidewire for use in guiding the crossing catheter through the vasculature of the patient and into the left ventricle. The retainer is preferably "c" shaped and comprises two prongs having ends connected by an intermediate member.

The present invention also includes a method for the percutaneous treatment of mitral valve regurgitation by reshaping a mitral valve annulus through a venous access site in a patient including the steps of accessing the right atrium through the venous access site with a transseptal access catheter; puncturing the septum using the transseptal access catheter; advancing the deflectable guide catheter over the transseptal access catheter through the transseptal puncture into the left atrium; withdrawing the transseptal access catheter from the patient; positioning the deflectable guide catheter with the distal opening pointing toward the mitral valve annulus; introducing a plication device into the venous access site through the lumen of the deflectable guide catheter and advancing the plication device out the distal opening of the deflectable guide catheter; positioning the plication device at a first position at or near the annulus of the mitral valve in the left atrium; plicating a first portion of tissue of the mitral valve using the plication device to create a first tissue plication; and applying a retainer to the first tissue plication.

The transseptal method may further include the steps of examining the first tissue plication using an imaging method to produce an image of the mitral valve; and, determining if the plication is acceptable prior to the step of applying the retainer; releasing the plication if the plication is determined not to be appropriate at the examining step; repositioning the plication device at a second position at or near the mitral valve annulus; plicating a first portion of tissue of the mitral valve at or near the annulus using the plication device to create a first tissue plication; determining if the first tissue plication as retained by the retainer sufficiently reshapes the mitral valve annulus to treat the mitral valve regurgitation; repositioning the deflectable guide catheter to a second position at or near the mitral valve annulus; introducing a second plication device or using a reloaded multi-retainer plication device in the delivery guide catheter and positioning the second plication device at or near the mitral valve annulus; plicating a second portion of tissue of the mitral valve at or near the annulus using the plication device to create a second tissue plication; and; applying a retainer to the second tissue plication. The method concludes with the withdrawal of the deflectable guide catheter and the plication device and closing the venous access site.

BRIEF DESCRIPTION OF THE DRAWINGS

FIG. 4 is a perspective view of a crossing catheter for use in treating mitral valve regurgitation in accordance with the present invention.

FIG. 5 is a cutaway view of a portion of the body of the crossing catheter of FIG. 4.

FIG. 6 is an elevational view of a deflecting guide catheter for use in treating mitral valve regurgitation in accordance with the present invention.

FIGS. 7A and 7B are an exploded view and a perspective view respectively of the components of a handle for the deflecting guide catheter of FIG. 6.

FIG. 15 is a perspective view of a retainer for use in a plication device for use in the treatment of mitral valve regurgitation in accordance with the present invention.

DETAILED DESCRIPTION OF THE INVENTION

Figure 1A:
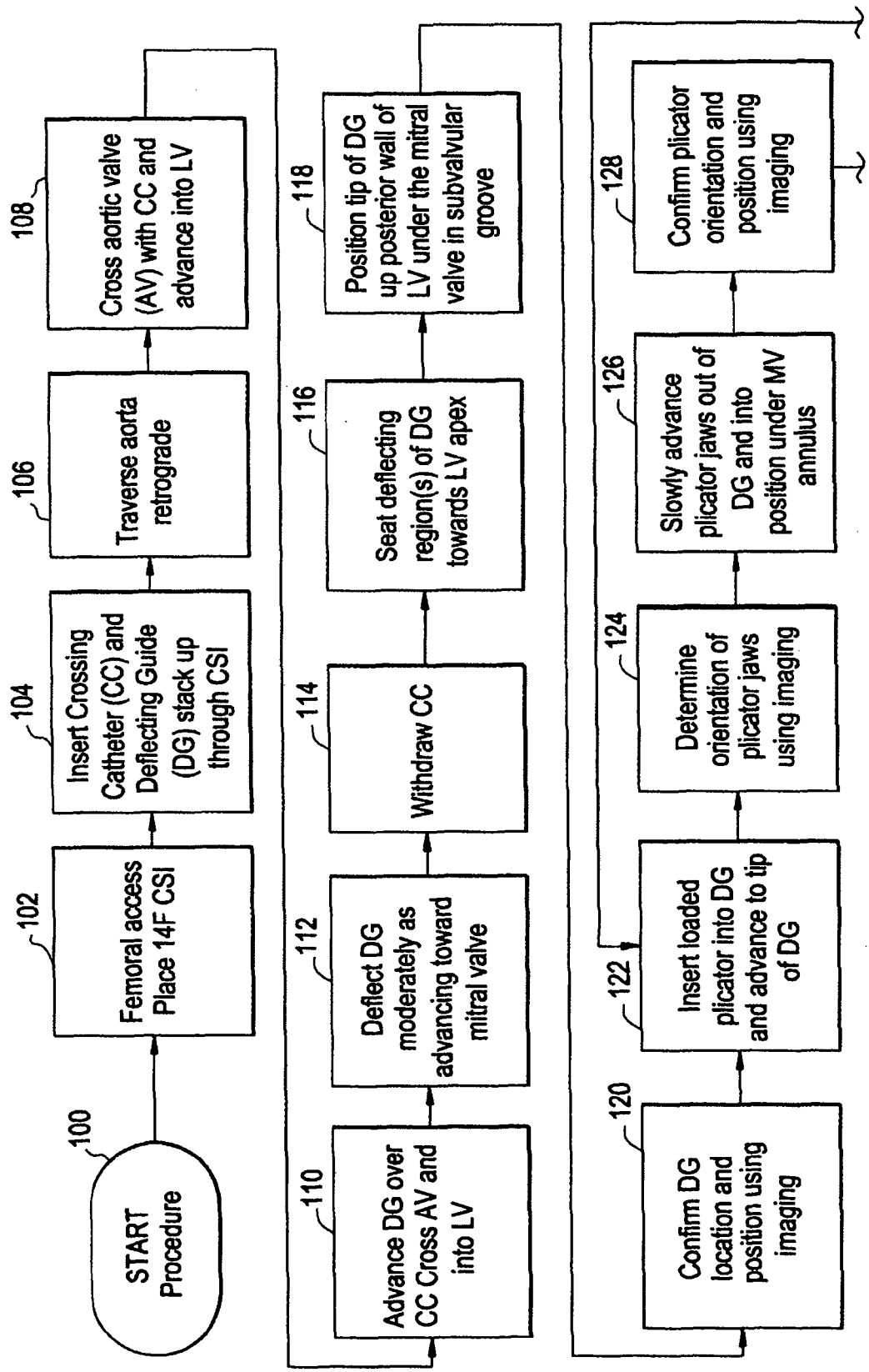
FIGS. 1A and 1B are a flow diagram describing the method of treating mitral valve regurgitation in accordance with the present invention.
Figure 1B:
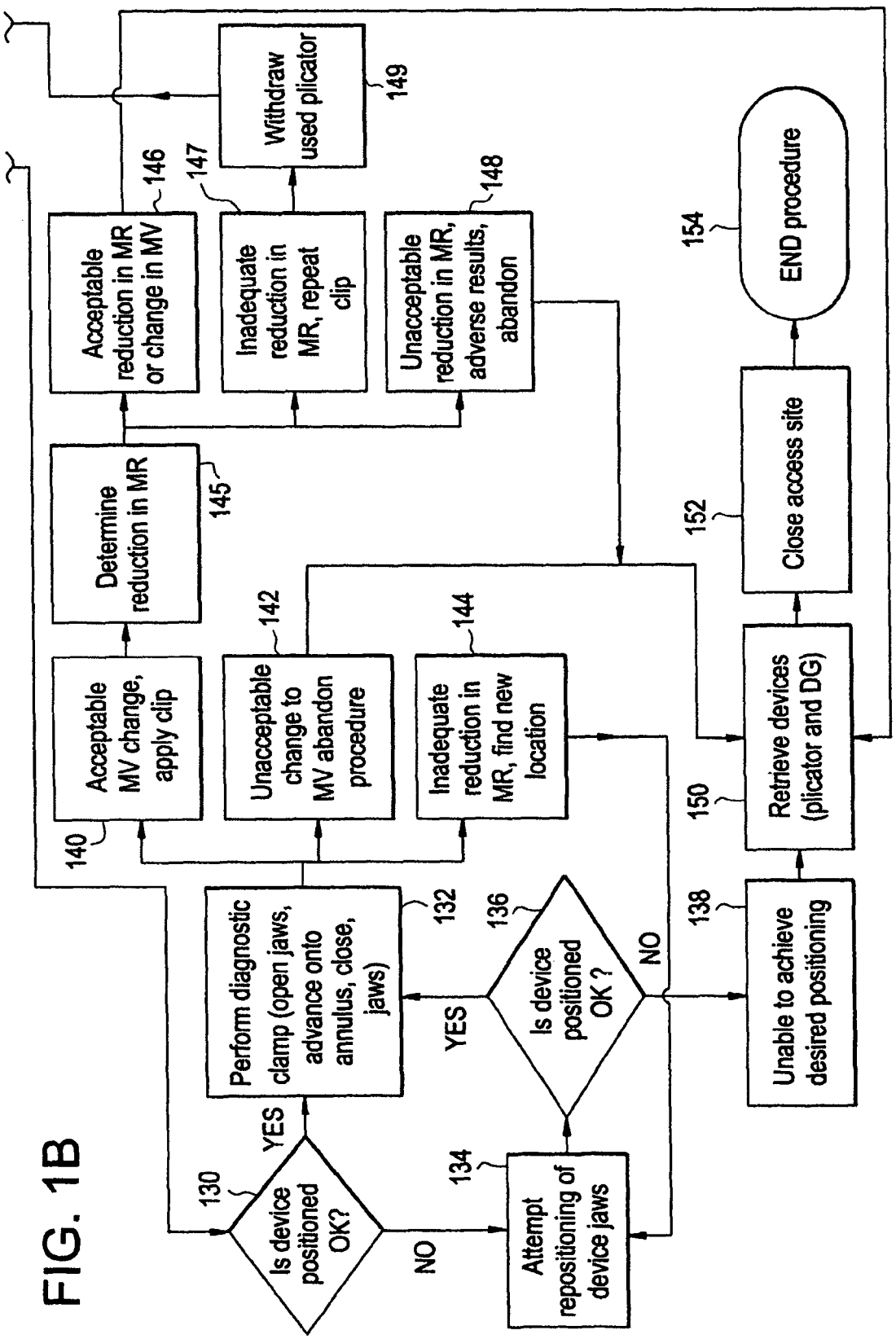
Figure 2A:
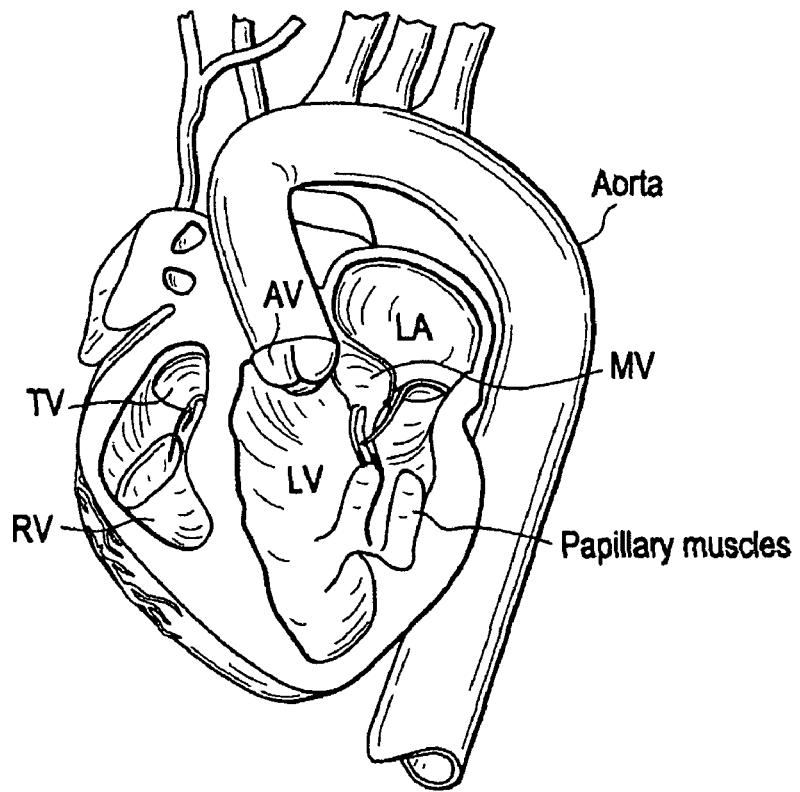
FIGS. 2A-H depict the stages of the various steps of the method of treating mitral valve regurgitation in accordance with the present invention.
Figure 2B:
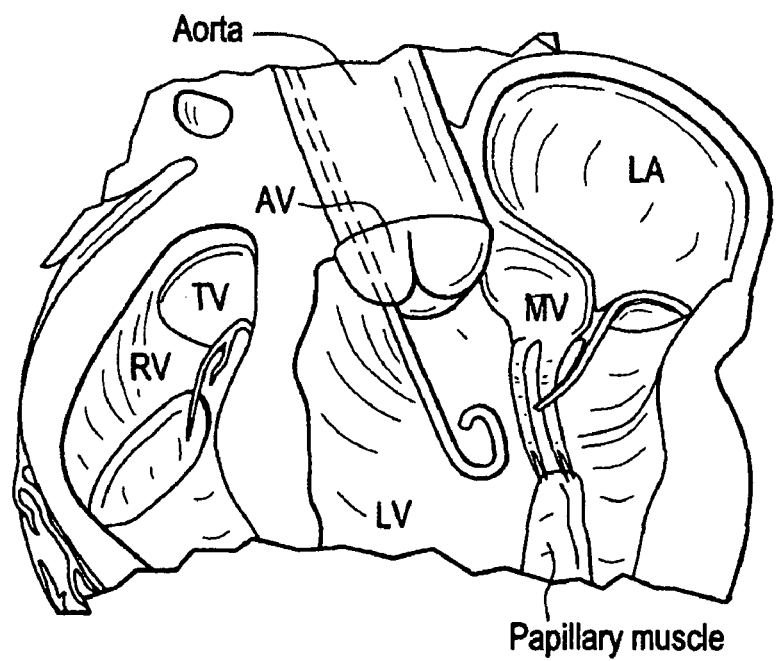
Figure 2C:
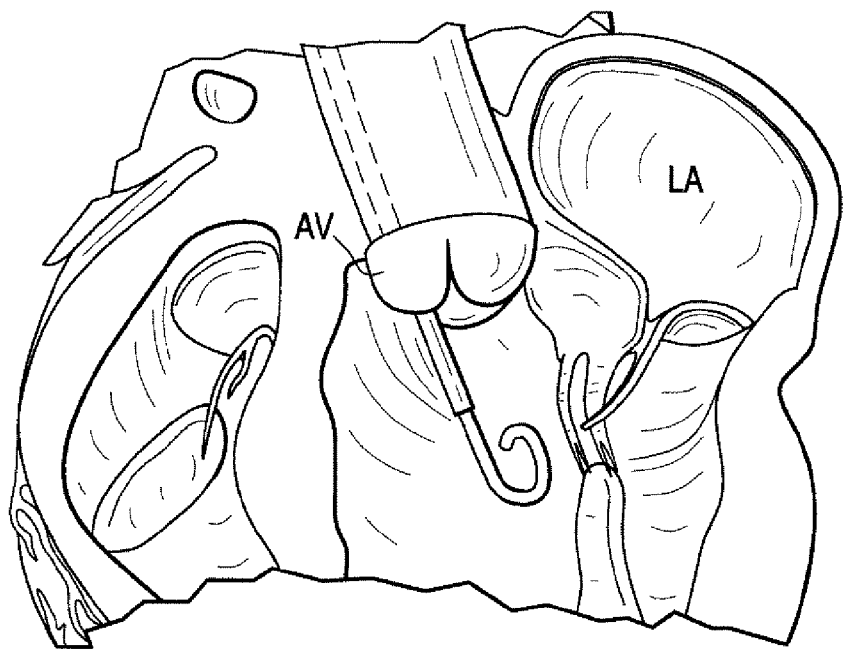
Figure 2D:
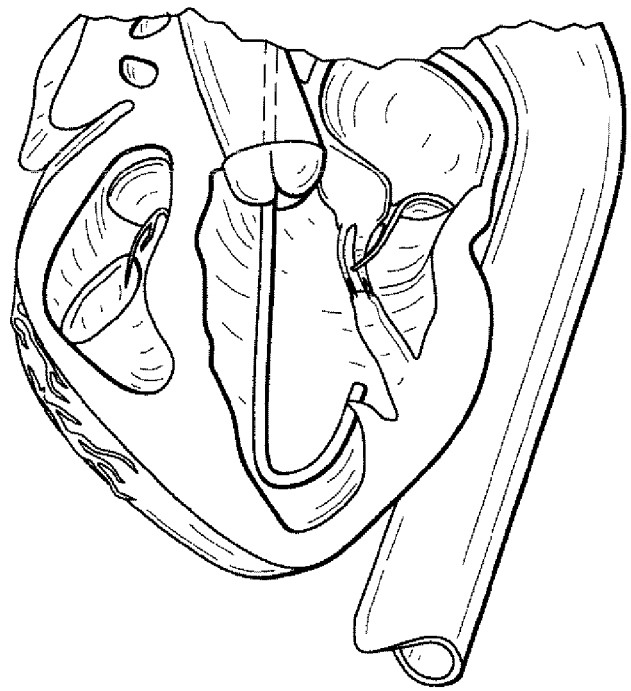

FIG. 1 is a flow diagram depicting a method of providing direct plication annuloplasty to the mitral valve in a heart such as that depicted in FIG. 2A in accordance with the present invention. At step 100 the procedure begins with a puncture for access to the femoral artery using standard techniques. At step 102 the physician or other practitioner places a catheter sheath introducer (CSI) into the femoral access point using standard techniques. Any known CSI may be used in the procedure with the preferable size being approximately 14 french. At step 104 a crossing catheter, preferably prolapseable or having a curved tip, and a deflecting guide catheter are inserted together in a "stack" formation through the CSI. Alternatively, the deflecting guide catheter is inserted through the CSI without a crossing catheter although the use of a crossing catheter is the preferred method. The crossing catheter is described herein in greater detail with respect to FIGS. 4 and 5 below and the deflecting guide catheter is described herein in greater detail with respect to FIGS. 6 to 11. The stacked crossing catheter and deflecting guide catheter are advanced through the arterial system of the patient traversing the aorta of the patient in a retrograde manner at step 106. At step 108 the aortic valve (AV) is crossed with the crossing catheter and the crossing catheter is advanced into the left ventricle (LV) as depicted in FIG. 2B. At step 110 the deflecting guide catheter is advanced over the crossing catheter through the aortic valve and into the left ventricle as depicted in FIG. 2C. The deflecting guide catheter is deflected in a somewhat retroflexed manner as it is advanced approximately toward the mitral valve at step 112 as depicted in FIG. 2D and the crossing catheter is withdrawn at step 114.

A guidewire may also be used with the crossing catheter and deflecting guide catheter in a three-element stack inserted in the CSI. If a guidewire is used it is advanced first through the arterial system and over the aortic arch followed by the combined stack of the crossing catheter and the deflecting guide catheter. The guidewire is introduced first through the aortic valve followed by the crossing catheter which is preferably oriented into a position between the papillary muscles although this is not necessary. The procedure then continues as in steps 110 and 112 above with the guidewire removed simultaneously with the crossing catheter at step 114.

Figure 2E:
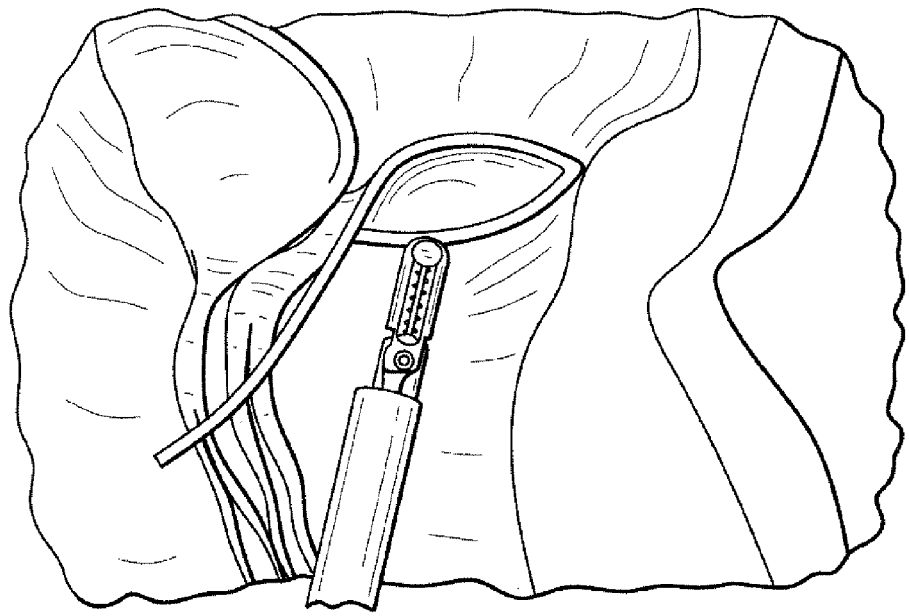
Figure 3:
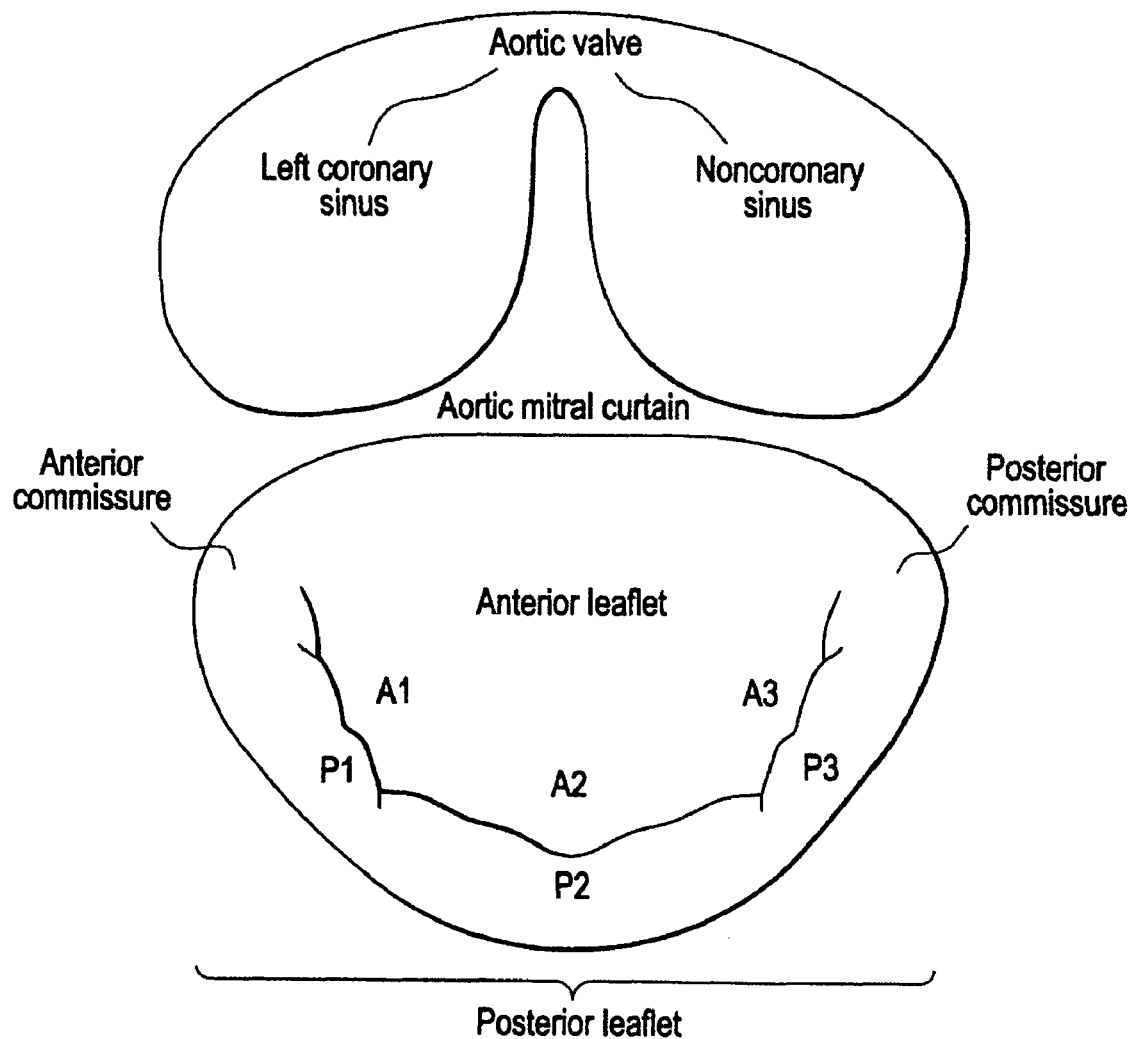
FIG. 3 depicts the plication regions in the method of treating mitral valve regurgitation in accordance with the present invention.
Figure 7B:
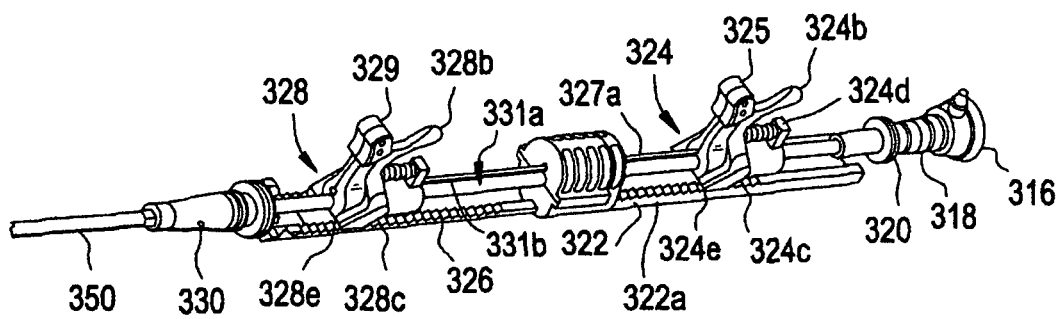

Whether or not a guidewire has been used, the procedure continues with step 116 where a region of the deflecting guide catheter is seated toward the mitral valve in the apex of the left ventricle as in FIG. 2E. At step 118, the tip of the deflecting guide catheter is advanced up the posterior wall of the left ventricle to a position under the mitral valve, preferably initially placed in the subvalvular groove in the P2 region of the as shown in FIG. 3. The term "annulus" is meant to include regions at or near the annulus. At step 120 the position of the tip of the deflecting guide catheter is confirmed by using an imaging method such as fluoroscopy. If fluoroscopy is used one view maybe sufficient but it is preferable in most cases to use two views to confirm proper placement of the deflecting guide catheter in the P2 region of the mitral valve annulus. P2 is the likely target region for a first retainer although depending on the geometery of the mitral valve the first retainer may be placed in region P1 or region P3. Additional retainers may need to be placed in the same or other regions.

At step 122 a plication device 400 loaded with one or more retainers is inserted into the deflecting guide catheter and advanced to the tip of the deflecting guide catheter. A plication device for use in this method is described in greater detail herein with respect to FIGS. 12 through 14H. At step 124 the rotational orientation of the jaws of the plication device is determined using an imaging method and the jaws are placed in the correct orientation. The preferable rotational orientation for the jaws of the plication device is such that both tips of the jaws once opened would represent a "chord" of the arc defined by the mitral valve annulus when pushed into contact with the annulus. Next, at step 126 the plication device is advanced out of the end of the deflecting guide catheter into position under the annulus of the mitral valve as depicted in FIG. 2E. The orientation and position of the plication device is reconfirmed at step 128 using an imaging method. Again, if fluoroscopy is used as the imaging method, at least one and preferably two views are be used to confirm orientation and placement of the jaws of the plication device. An injection of a known contrast agent either using a separate contrast catheter or through the deflecting guide catheter may be used to help define the line of the annulus as viewed under fluoroscopy. At step 130 a decision is made by the physician whether or not the jaws of the plication device are properly positioned. If the plication device is not correctly positioned then at step 134 an attempt is made to reposition the jaws of the plication device. At step 136 the position of the plication device is evaluated again using an imaging method as described previously and in more detail below. If the plication device is positioned correctly then step 132 and onward are performed as discussed below. If the plication device is not positioned properly after at least one attempt at repositioning at step 134 then step 138 results in a determination that the plication device cannot achieve a desired position and the plication device and deflectable guide catheter are withdrawn from the patient at step 150.

Figure 2F:
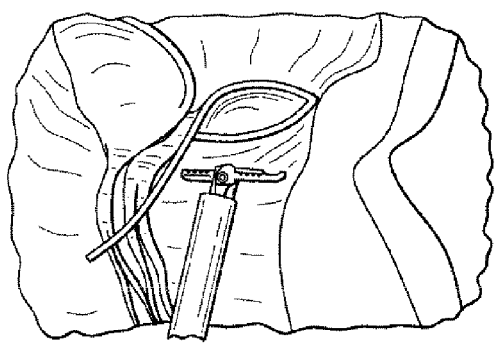
Figure 2G:
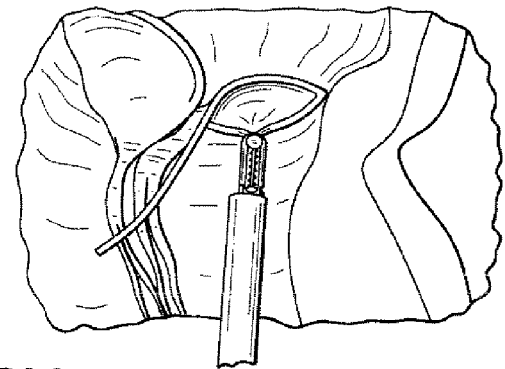
Figure 2H:
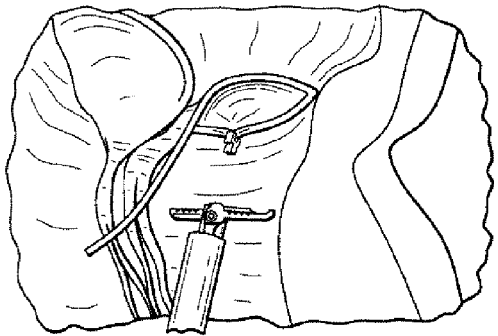

If the jaws are properly positioned, a diagnostic clamp or plication is performed at step 132. As part of the diagnostic clamping (or plication), the jaws of the plication device are opened as depicted in FIG. 2F, the plication device is advanced onto the tissue of the annulus of the mitral valve and the jaws are closed as depicted in FIG. 2G. The diagnostic plication is evaluated at steps 140, 142 and 144. If the diagnostic plication results in an acceptable change in the mitral valve annulus and/or an acceptable reduction in mitral valve regurgitation then a retainer is applied using the plication device at step 140 and the plication device is released as depicted in FIG. 2H. Embodiments of a retainer that may be applied to the tissue are described in greater detail herein with respect to FIG. 15. At step 142, if the diagnostic plication results in an unacceptable change to the mitral valve then the procedure is abandoned and both the plication device and the deflectable guide catheter are withdrawn from the patient at step 150. At step 144, if the diagnostic plication results in an insufficent or inadequate reduction in mitral valve regurgitation (MR) and/or insufficient or inadequate change in the mitral valve then the diagnostic plication is released and an attempt to reposition the jaws of the plication device is performed at step 134.

If the change to the mitral valve is acceptable and a retainer has been applied, then at step 145 a determination regarding the impact of the plication on the regurgitation of the mitral valve is made using a method of imaging the flow of blood through the valve such as Doppler echocardiography. At steps 146, 147 and 148 various decisions are made regarding the procedure and continuation of the procedure. At step 146, if the determination is made that there has been an acceptable total reduction in mitral valve regurgitation and/or acceptable change in the mitral valve then the procedure branches to step 150 with the retrieval of the plication device and the deflecting guide catheter. If the total change to mitral valve regurgitation is inadequate or insufficient and/or change to the mitral valve is inadequate or insufficient (step 147) then the plication device currently in use is withdrawn if it is a single retainer device and an additional plication device is inserted and the procedure continues from step 122. If the plication device is a multi-retainer device then the procedure continues from step 124 without withdrawal of the plication device. If the determination regarding the impact of the plication on mitral valve regurgitation results in a finding of an adverse result at step 148 then the procedure will likely be abandoned and both the plication device and deflecting guide catheter are removed from the patient at step 150. After removal of the plication device and the deflecting guide catheter, the catheter sheath introducer is removed and the access site is closed at step 152 using known methods.

In the above method various imaging modalities may be used to determine proper placement of the plication device under the mitral valve annulus. Fluoroscopy is one real-time imaging modality that is useful, preferably, where images are taken in at least two planes. Radiopaque markers placed on the distal end of the plication device and/or deflecting guide will aid in determining proper placement. A three-dimensional profile of the plication device can be created using x-ray images acquired in at least two planar projections in real-time. Alternatively, rotational angiographic imaging may be used. Additionally, registering pre-acquired CT or MRI image data with the fluoroscopic image will provide additional anatomic data to the physician to aid proper placement of the plication device and retainer or retainer. Similarly, a three-dimensional real-time ultrasound image acquired in real-time may be registered with the fluoroscopic image.

Another imaging modality useful for this purpose is intracardiac echocardiography (ICE) used to produce an ICE image. The ICE image may be produced by an ICE catheter placed inside one of the chambers of the heart such as the right ventricle, left ventricle, left atrium or the right atrium. Alternatively, the ICE catheter could be placed inside on of the great vessels of the heart of the patient. The ICE catheter may also be placed on the epicardial or pericardial sack surfaces of the heart via a minimally invasive approach such as a sub-xiphoid approach.

No matter the modality used, the images of the mitral valve should be taken synchronized to the cardiac cycle.

Various imaging modalities are also useful in determining whether the plication achieves the desired impact on the function of the mitral valve in real-time or near real-time prior to applying the retainer to the plication. Real-time means that the latency period is acceptable to perform the procedure and is preferably no more than 500 milliseconds. Color Doppler ultrasound imaging may be used for such a purpose with or without an ultrasound contrast agent being administered to the patient. Alternatively, x-ray fluoroscopy could be used in determining the impact of a plication on mitral valve regurgitation by using an x-ray contrast bolus injection into one of the chambers of the heart, preferably the left ventricle. Bi-planar angiographic imaging or intra-chamber optical imaging may also be used. If intra-chamber optical imaging is used it is preferable that the deflecting guide catheter further comprise an optical imaging system particularly one that operates in infrared wavelengths.

Determining a location for the first tissue plication may be based on an optimization plan generated using a three-dimensional functional numerical simulation based on imaging data generated by one or more of the aforementioned imaging method. For example, by analyzing the distribution of annular tissue relative to the location of the primary regurgitant flow through the valve, a primary target for initial plication therapy may be determined. It may be desirable to place the plication at the location of greatest distortion of the annulus due to the pathology of the patient's heart. The generation of the optimization plan may be performed prior to step of inserting the crossing catheter. The generation of the optimization plan may be performed after the step of applying a retainer to the first tissue plication in order to determine the preferred location for subsequent plication or plications.

Alternatively, the plications could be made on the atrial surface if a transseptal approach is used. This can be accomplished by accessing the right atrium using SVC or IVC venous approaches. Then access the left atrium is accomplished using a standard transseptal puncture/access kit such as a Brockenbrough transseptal needle kit. The deflecting guide catheter would then be introduced through the puncture and deflected such that the tip pointed towards the annulus of the mitral valve. The subsequent steps and devices for a plication annuloplasty procedure would then be the substantially the same as set forth above except that the approach is from the atrial side of the mitral valve rather than the underside.

The above method is implemented using a multi-component system comprising a crossing catheter 200, a deflecting guide catheter 300, and a plication device 400 containing at least one plication retainer 500. FIG. 4 is a perspective view of a crossing catheter 200 for use in the procedure described in the present application. Crossing catheter 200 is comprised of a body portion 210 having a proximal end 210a and a distal end 210b. Connected to proximal end 210a are a female luer lock 216 and a Tuohy-Borst hemostasis valve 214. At the distal end 210b portion is attached which is preferably a pigtail 218 or has a "J" configuration (not shown). Pigtail 218 is approximately 2.0 centimeters or less in diameter. In FIG. 4 pigtail 218 is attached to body portion 210 at a splice location that is approximately 4 centimeters from the distal end of the device. Pigtail 218 is attached to body portion 210 using heat bonding as the body portion 210 and pigtail 218 re made from the same or similar material. Pigtail 218 is comprised of a polymer, prefereably, Pebax® polyether block amide having a durometer of approximately 55D if comprised of one layer or two layers having durometers of approximately 40D in the outer layer and 55D in the inner layer. Body portion 210 may be comprised of one layer having a durometer between 55D and 72D or may have two layers. If two layers are used the preferred durometers are 70D for the outside and 63D for the inside. The total length of the body portion and pigtail together is approximately 149 centimeters and should extend beyond the deflecting guide catheter when fully inserted into the deflecting guide catheter thus the length of the crossing catheter may vary depending on the length of the deflecting guide catheter used. The location at which the pigtail may be attached to the body portion may also vary from 3 centimeters to approximately 44.5 centimeters from the distal tip of the crossing catheter 200. The crossing catheter may also be comprised of one material from the body portion through the pigtail. In such a case the use of an outer material with a durometer of 55D and an inner material with a durometer of 40D is preferred. A flat wire braid 212 of flat wires of approximately 0.001" by 0.003" may be embedded in the polymer comprising the proximal portion of body portion 210 in order to provide extra stiffness and torqueability. An inner layer 211 of PTFE provide a lubricious inner coating and a separation between the polymer and the inner lumen. The stiffness of the pigtail portion of the crossing catheter is chosen so that a standard guidewire such as the Cordis Emerald 0.035" guidewire will open up the pigtail yet will return to the pigtail shape when retracted. Such a guidewire is placed in the guidewire lumen defined by the inner layer 211 of the crossing catheter and should extend through the entire length of the crossing catheter.

Crossing catheter 200 may be used with or without a guidewire as described above and is preferably used in conjunction with the deflecting guide catheter depicted in FIGS. 6 through 10A-C. Deflecting guide catheter 300 is comprised of a handle 310 and a body portion 350. FIG. 7A is an exploded view of an embodiment of the handle 310 depicting the internal components of the handle and FIG. 7B is a perspective view of the internal components of handle 310 as assembled. Handle 310 is comprised of upper handle shell 312 and lower handle shell 314 which are made of a durable moldable polymeric material such as polycarbonate or other similar material and are designed to mate with one another in a snap fit arrangement. At the proximal end of handle 310 is a hemostasis valve 316 which is adapted to fit onto the proximal handle tip 318. Hemostasis valve 316 may be of any known design for such a valve such as a tuohy-borst type valve. Proximal actuator assembly 324 is comprised of a thumb actuator 324a that is adapted to be inserted through slot 313 in the upper handle shell 312. Optionally, a two-piece construction with a thumb cap 325 may be used to facilitate assembly if slot 313 is narrow. The thumb actuator 324a and optional thumb 325 cap are used to cause forward motion in the proximal direction of puller wire 327a. Such motion is retained as the prong or prongs 324e biased by spring 324d around pivot point axel pin 324c engages the teeth 322a in proximal rack 322. Such proximal motion of the proximal actuator assembly 324 and the associated puller wire 327a causes the deflection of the distal end of the deflecting guide catheter 300. If the user desires to have distal motion of the proximal actuator assembly 324 then the user pushers release trigger 324b which counters the bias of spring 324d thereby releasing prong or prongs 324e from engagement with the teeth 322a of the proximal rack 322. Proximal hypotube 331a provides a passage way for puller wire 327a and prevents kinking of the wire. Distal hypotube 331b is designed to telescope inside hypotube 331a. At the end of puller wire 327a are fixedly attached crimp tube 334a and a floating crimp tube stop 334b that prevents the crimp tube from being embedded in the proximal end of the actuator assembly. The user may then move the actuator assembly distally thereby changing the deflection of the distal end of the deflecting guide catheter. Movement of the actuator assembly may be made by the physician using something other than his or her thumb and the terms "thumb actuator" and "thumb cap" are not meant to be limiting.

Handle 310 further comprises a distal actuator assembly 328 having a similar thumb actuator 328a, release trigger 324b, axel pin 324c, spring 328d and prong 328e. Optional thumb cap 329 is affixed over thumb actuator 328a. The distal actuator assembly 328 is connected to a second pullerwire 327b (shown in FIG. 11) that enables the user to cause deflection of the distal end of the deflecting guide catheter. In a preferred embodiment the first and second puller wires are attached (through known methods and means such as welding, brazing or adhesives) to anchor bands 385a and 385b that are embedded in the distal region 360 of the body portion 350 of the deflecting guide. The puller wires and their respective anchor band connection points may also be arranged so that they are not next to one another (in an axial manner) but so that each provides motion of the distal end in another plane or in the other direction within the same plane. Also, the second puller wire and actuator are not necessary if it is only necessary to provide one type of movement in the deflecting guide catheter. Correspondingly, if greater than two types of deflection are required, additional thumb actuator assemblies coupled to puller wires and anchor bands may be added in a similar manner to the catheter. The second distal actuator assembly has the same components as functions in the same manner as the proximal actuator assembly. The primary difference is that the distal actuator assembly 328 requires a passageway for passage of the first puller wire 327a through the distal assembly which passage is aided by hypotube 331b. The second puller wire 327b ends at the distal end with a similar crimp tube 335a and crimp tube stop 335b. Nose cone 330 provides a transition between the handle shell 312/314 and the proximal region 390 of the body portion 350. Acuator assemblies 324 and 328 and racks 322 and 326 are comprised of a polymeric material such as polycarbonate. Such assemblies could be made of machined or molded metal, such as aluminum, although that would result in a higher cost and weight device. Racks 322 and 326 with teeth 322a and 326a may be separate components or may preferably be molded into the lower handle shell 314 as depicted in the alternative embodiment shown in FIG. 11. Handle insert 338 is used as a divider between the two racks 322 and 326 and provides a support for proximal hypotube 331a. Puller wires 327a and 327b are preferably high tensile strength 304 stainless steel (e.g. tensile strength greater than 300 ksi) but may also be made of other high strength materials such as MP35N, other stainless steel, or woven fibers such as Kevlar or Vectran.

Puller wires 327a and 327b are preferably a single, solid core high tensile strength 304 stainless steel wire (e.g. tensile strength greater than 300 ksi) of approximately 0.008" in diameter but may also be made of other high strength materials such as MP35N, other stainless steel, or woven fibers such as Kevlar or Vectran. At the distal end of each puller wire is an anchor band 385a or 385b that is embedded in the wall of the catheter body at the point of anchoring. Changing the location of the anchor band along the axial length of the catheter body will change the deflection profile of the deflectable guide catheter.

Figure 8:
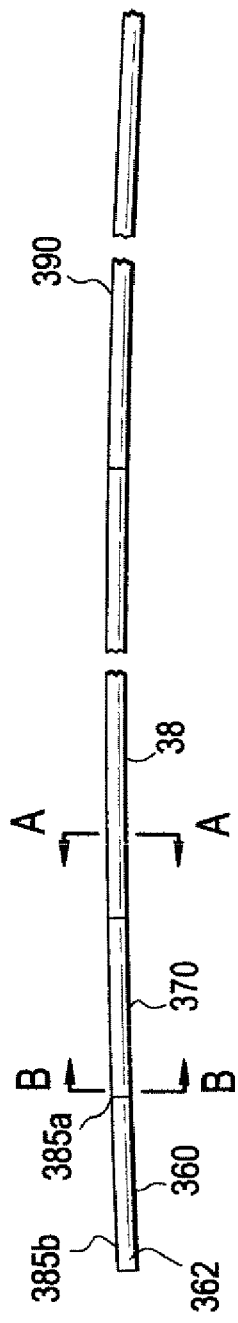
FIG. 8 is an elevational view of the body portion of the deflecting guide catheter of FIG. 6.
Figure 9B:
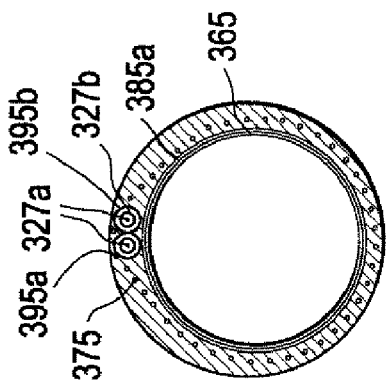
FIGS. 9A and 9B are cross-sectional views of the body portion of the deflecting guide catheter of FIG. 8 taken through lines A and B respectively.
Figure 9A:
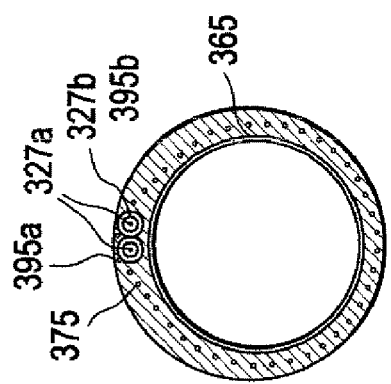
Figure 11:
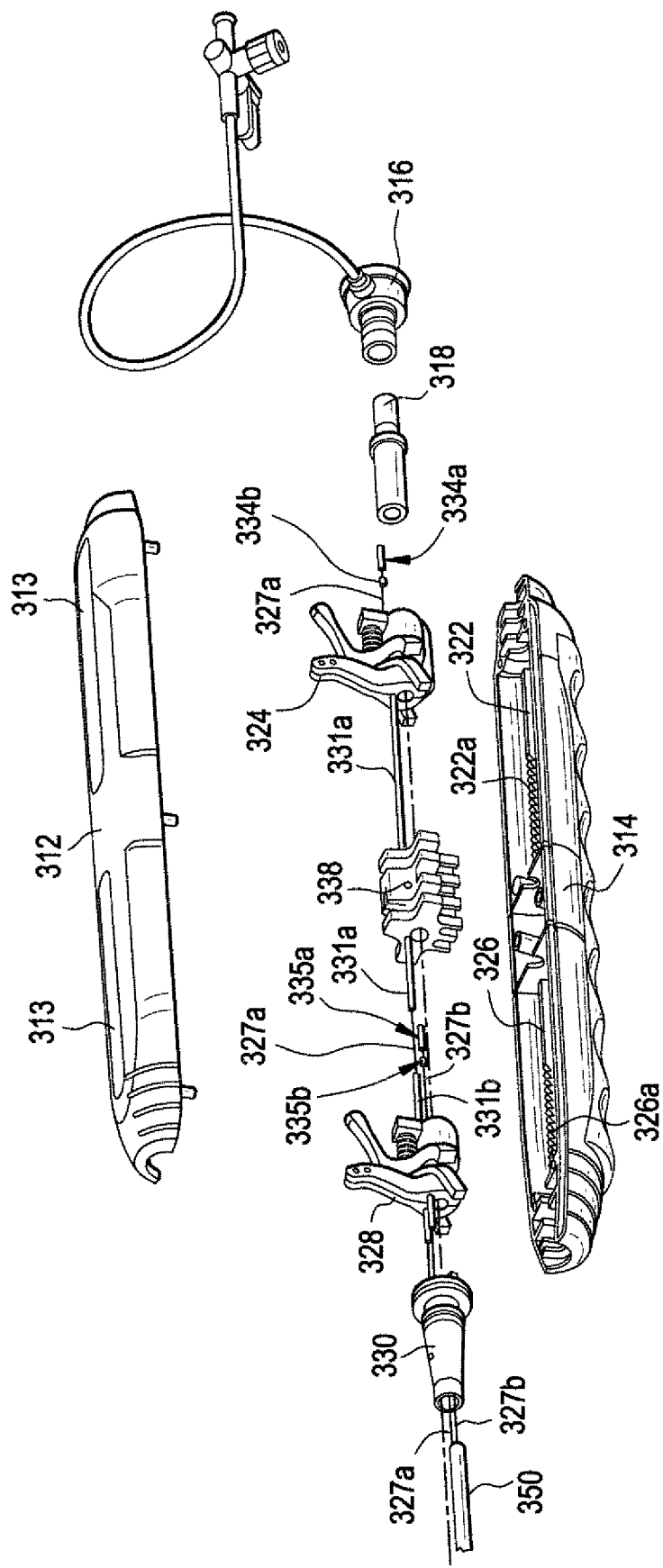
FIG. 11 is an exploded perspective view of another embodiment of the handle and internal components used in a deflecting guide catheter in accordance with the present invention.

Body portion 350 of deflecting guide catheter 300 is depicted in FIG. 8 and FIGS. 9A and 9B. Body portion is separated into four regions: distal region 360, intermediate distal region 370, main intermediate region 380 and proximal region 390. Distal region 360 at the distal end is approximately 3.5 centimeters in length and is made of a polymeric material such as Pebax with a durometer of between 25D and 40D and preferably 35D. A radiopaque material such as bismuth subcarbonate is added to the material in distal region 360 to enable the distal region 360 of the deflecting guide catheter 300 appear in fluoroscopy and other imaging procedures. The wall thickness in the distal region 360 is between approximately 0.012 and 0.014 inches. The anchor band 385a for the first puller wire is embedded near the distal end of distal region 360 and the anchor band 385b for the second puller wire is embedded near the proximal end of distal region 360 or at the distal end of region 370. The anchor bands are preferable placed between the lubricious liner 365 and the braid 385 although it could be placed above the braid in an alternative embodiment. Each anchor band is made of 304 stainless steel and each puller wire is attached to its respective anchor band using welding or other means for joining metal that is known in the art. The internal diameter of distal region 360 as well as the entire body portion is defined by a lubricious liner 365 preferably PTFE that has an interior diameter of approximately 0.127 inches and is approximately 0.002 inches thick. The outer diameter of distal region 360 is approximately 0.172 inches between the anchor bands and approximately 0.176 inches at the location of the distal band. A braid 375 of wires having a diameter between 0.0025 and 0.003 inches in a 1 over 1, 1 over 2 under 2 or 2 over 2 pattern is embedded in the polymeric wall of the catheter from the proximal region 390 to the distal region 360. At the distal end of the distal region 360 of deflecting guide 300 is an extruded atraumatic tip 362 comprised of 33.5% 25D Pebax, 6.4% 55D Pebax and 60% bismuth subcarbonate and having a slight taper toward its distal end. The atraumatic tip is optional although preferred in order to avoid tissue damage during insertion in the vessels of the patient.

Intermediate distal region 370 is comprised of the same type of polymeric material but has a higher durometer of between 35D and 55D to provide a stiffer region. Intermediate distal region 370 is between approximately 2.8 and 4.0 centimeters in length and contains the same lubricious liner 365 and wire braid 375 as the distal region. The wall thickness in the intermediate distal region is similarly between 0.012 and 0.014 inches and the outer diameter is approximately 0.172 inches. Main intermediate region 380 has a slightly smaller outer diameter at 0.166 inches but has the same lubricious liner and braid as the other regions. The main difference in this region is the higher durometer of between 55D and 63D for the polymeric material used in order to provide increasing stiffness. The main intermediate region is approximately 20 to 28 centimeters in length, preferably 20 centimeters. Proximal region 390 has a similar composition in that the outer diameter is the same as the immediately prior region. The durometer in this region is increased to approximately 72D providing even greater stiffness and the length of this region is approximately 73 to 88 centimeters, preferably 88 centimeters. The lubricious layer 365 and braid 375 are the same.

Figure 10A:
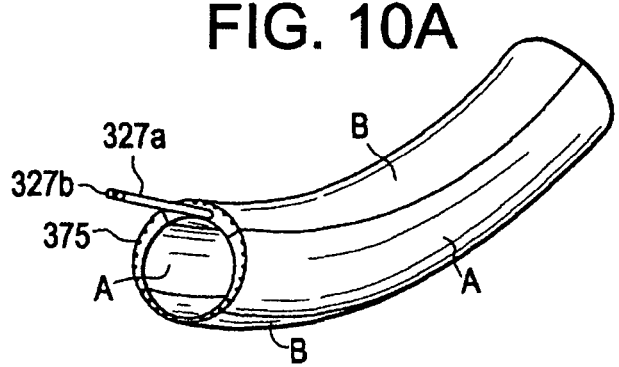
FIGS. 10A-10C are perspective views of the body portion of other embodiments of a deflecting guide catheter for use in treating mitral valve regurgitation
Figure 10B:
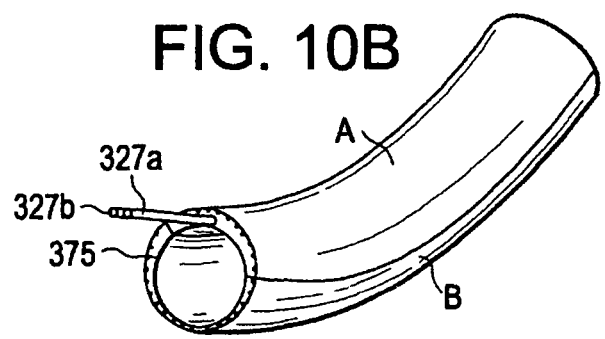
Figure 10C:
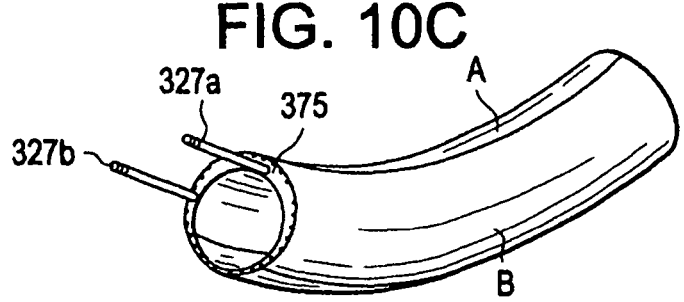

From the proximal region 390 through the body portion 350 until the position of first and second anchor bands 385a/385b run two wire or braid reinforced tubes 395a/395b of approximately 0.0088 inches in internal diameter which house the first and second puller wires respectively. Various modifications can be made to the deflecting guide catheter if different characteristics are desired. One puller wire, anchor band and reinforced tube could be used instead of two. The braid may be changed to a different size wire and braid type. The polymeric material of the outer body may be varied as depicted in FIGS. 10A-10C. In FIG. 10A materials having two different durometers are used in an alternating fashion. Material A is used in two circumferential portions opposite one another while material B is used in two other opposing circumferential portions. The durometer of material A may be greater than the durometer of material B or vice versa depending on the deflection characteristics desired. Use of two different durometer materials in such a way provides the benefit of balancing the ability or ease of the catheters to deflect in a particular direction with the requirement for lateral stiffness. In FIG. 10B two circumferential portions of material A and material B are used to provide a certain desired deflection characteristic. In FIG. 10C the use of two different durometer materials is used in conjunction with placement of the puller wires 327a and 327b at different places along the circumference of the body portion. In the configuration in FIG. 10C the distal end of the deflecting guide catheter would deflect in two different planes substantially perpendicular to one another. One should note that it is not require to use two different materials or durometer types around the circumference of the outer body in order to get different planes of deflection. The plane of deflection is primarily determined by the relative placement of the puller wire lumens.

The deflecting guide catheter may further comprise a magnetic based location sensor such as those manufactured by Biosense Webster for sensing the location and orientation (six degrees of freedom) of the distal end of the deflecting guide catheter and for providing location information that may be registered with other preaquired or real-time images or otherwise used to depict the location of the distal end of the deflecting guide catheter on a real-time display map of the heart. Systems such as the Carto® system produced by Biosense Webster would be useful for this purpose.

Figure 12:
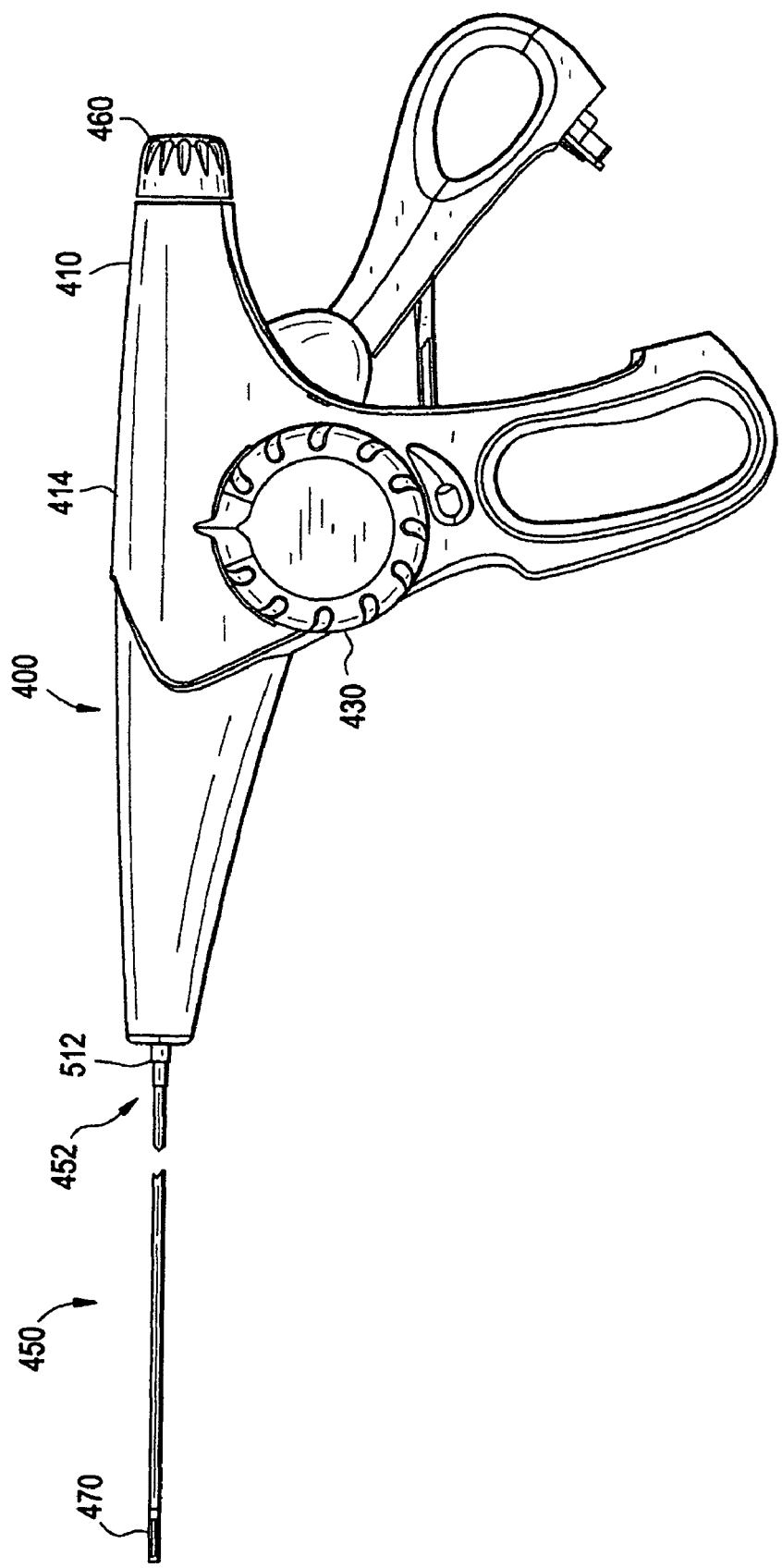
FIG. 12 is an elevational view of a plication device for use in treating mitral valve regurgitation in accordance with the present invention.
Figure 13:
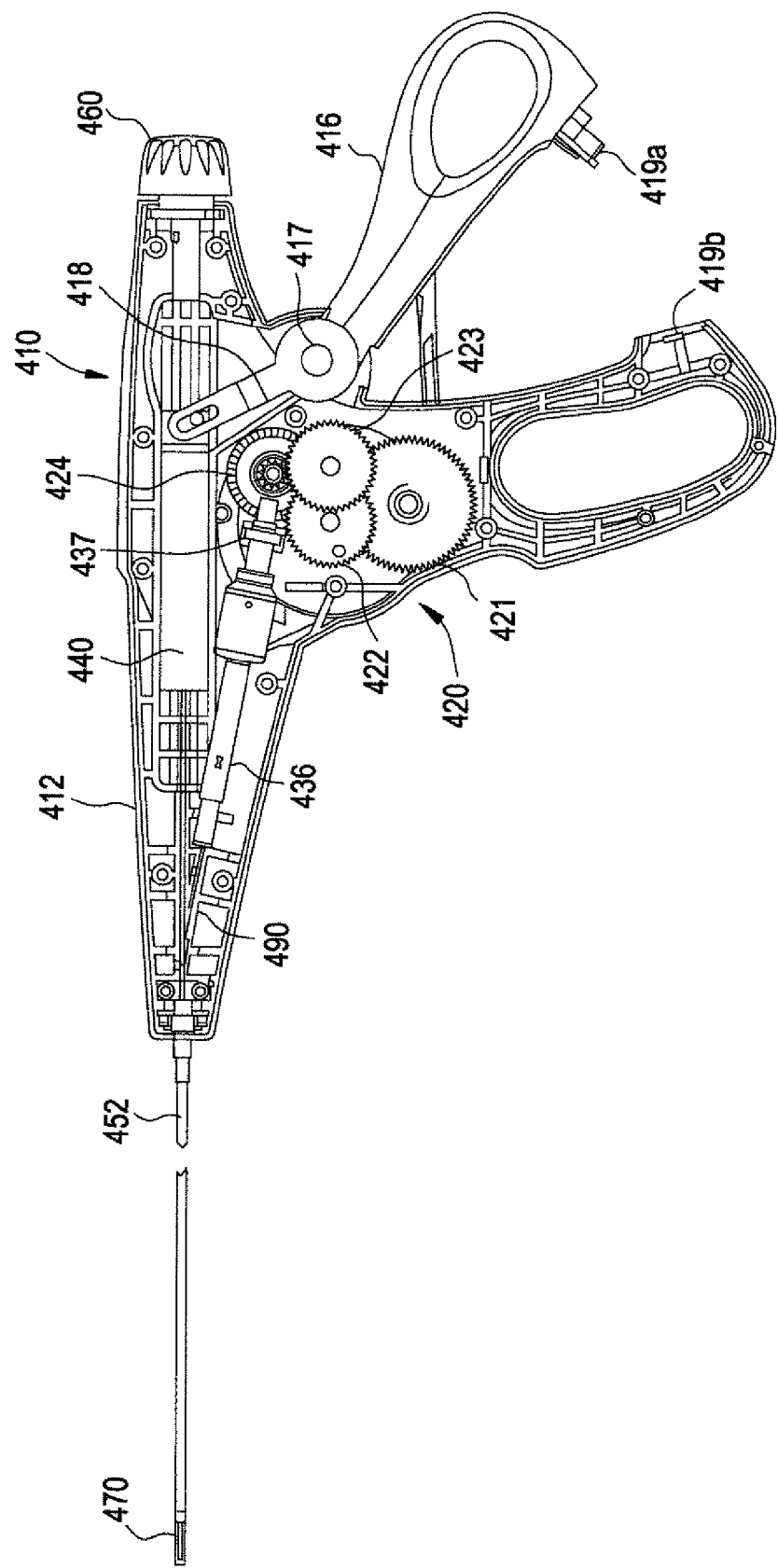
FIG. 13 is an elevational view of the plication device of FIG. 12 with a portion removed to expose the internal components.

FIG. 12 is an elevational view of a plication device 400 for use in the method of treating mitral valve regurgitation in accordance with the present invention. Plication device 400 is comprised of a handle assembly 410 and a distal assembly 450 having an elongate shaft 452 at the distal end of which are attached a plication assembly with an end effector 520. FIG. 13 is an elevational view of the internal components of the handle assembly 410. Handle assembly 410 is comprised of two polycarbonate shell portions—right handle shell 412 and left handle shell 414 that are adapted to house the internal components of the handle assembly. Internal to handle assembly 410 reside crank assembly 420 for advancing a retainer stored in the distal portion of the elongate shaft 452. The firing assembly 420 is comprised of counter gear 421, drive gear assembly 422, idle gear 423, and crown gear 424. Firing assembly 420 is coupled to the firing knob 430, shown in FIG. 12, which is rotatably coupled to left handle shell 414. While not shown, a second firing knob can be disposed on the opposed side of the handle assembly 410 to allow a user to selectively rotate either knob. Either firing knob further comprises a anti-backup leaf spring (not shown) that prevents the knob from turning in the reverse direction and a trigger lockout spring (not shown) that prevents the knob from turning until the trigger is fully closed or engaged. Continuing to refer to FIG. 13, the gears 421, 422, 423 and 424 of firing assembly 420 are configured to rotate in response to rotation of the firing knob 430. The gears communicate with one another to cause corresponding rotation of pinion assembly 437 and drive shaft 436. Drive shaft 436 is mated to a proximal end of firing control wire 490. End cap 460 has a plurality of ridges dispersed around it circumference to aid the grip of the user.

Figure 14G:
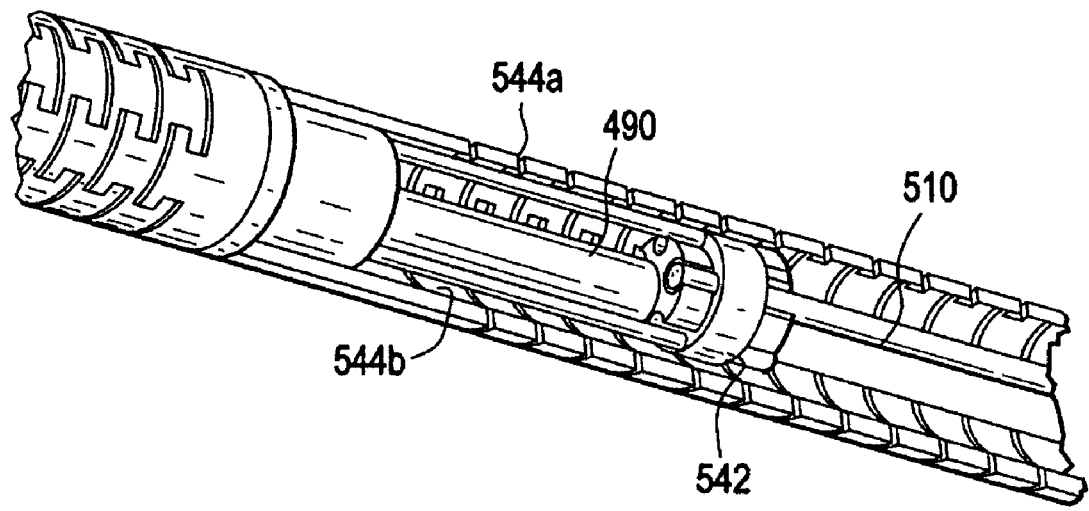
FIG. 14G is a detailed perspective view depicting the coupling of the end-effector control wire to the distal puller wires.
Figure 14H:
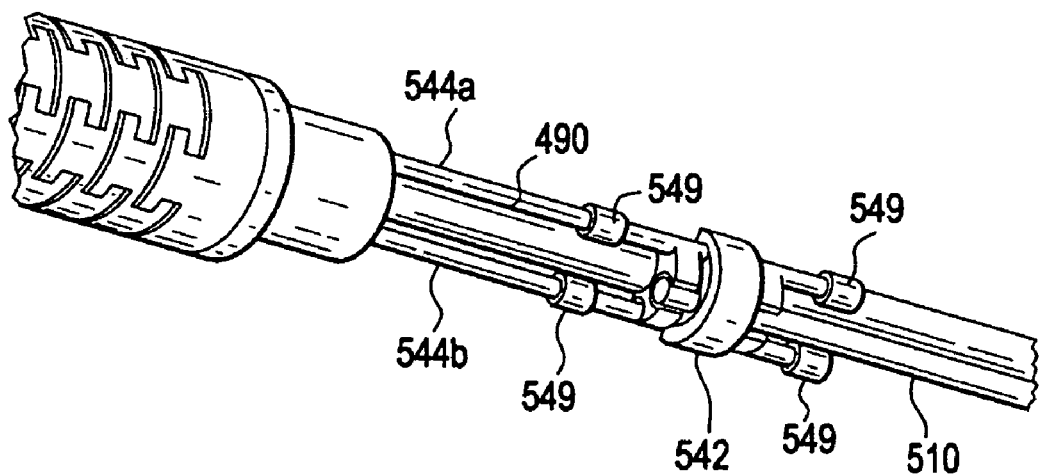
FIG. 14A is an elevational view of the plication device of FIGS. 12 and 13 from the shuttle assembly to the distal end.
FIG. 14B is a cross sectional view of the portion of the plication device of FIG. 14A taken through line A-A.
FIG. 14C is an enlarged view of proximal end section D of the cross-sectional view of the portion of the plication device of FIG. 14B.
FIG. 14D is an enlarged view of distal section C of the cross-sectional view of the portion of the plication device of FIG. 14B.
FIG. 14E is an enlarged view of the distal tip section B of the cross-sectional view of the portion of the plication device of FIG. 14B.
FIG. 14F is an enlarged planar view of the distal tip of the plication device of FIG. 14A.
FIG. 14 H is a detailed perspective view depicting the coupling of the end-effector control wire to the distal puller wires in an embodiment of the plication device having passive articulation.

In FIG. 13, the trigger 416 is pivotally mounted within the handle assembly 410 by a pivot pin 417, and includes a distal portion having a thumb grip formed therein and a proximal extension arm 418. The trigger 416 also includes a latch 419a that is adapted to be received in the latch receiver 419b in the handle assembly to lock the trigger into a closed position. The extension arm 418 is coupled to a shuttle assembly 440 that moves between proximal and distal positions within the housing assembly 410. The shuttle assembly 440 can have various configurations and it can include various features, such as an overload mechanism. The particular configuration of the shuttle assembly 440 is described in more detail in U.S. Patent Publication No. 2005/0277954 herein incorporated by reference. Some of the internal parts of the shuttle assembly 440 including spring pin 446, force limiting spring 442, spring caps 444a and 444b are shown in FIGS. 14A and 14B. As shown in FIG. 13, the shuttle assembly 440 is coupled to a proximal portion of end-effector control wire 510, which extends through the elongate shaft 452. The distal end of the end effector control wire 510 mates (preferably by welding) to wire connector 542, which is shown in FIG. 14D The wire connector 542 is positioned as shown in FIG. 14G proximal to the end effector 520, i.e., the clevis 522 and jaws 524a and 524b. Wire connector 542 is also welded to two parallel pull wires 544a and 544b that run from wire connector 542 through nut 550 and terminate in holes at the proximal end of jaws 524a and 524b respectively. Thus, wire connector 542 splits the force of end effector control wire 510 into two forces for controlling the opening and closing of the jaws. Other arrangements are possible if, for example, it would be desired to have one fixed jaw and one movable jaw rather than two movable jaws. It is also possible to have some passive articulation of the distal jaws 524a and 524b by having the pull wires 544a and 544b pass through wire connector 542 as depicted in FIG. 14H and placing a plurality of ferrules 549 in each pull wire 544a and 544b, one each proximally and distally of the wire connector 542 proximal end of each wire so that they may translate through the wire connector thereby providing flexibility at the distal tip of the device for improved maneuverability through tortuous anatomical pathways. Distal jaws 524a and 524b rotate around pivot point rivots 523a and 523b respectively.

The firing control wire 490 extends through the elongate shaft 452 and through a bore formed in the wire connector 542 and is threadably mated to a threaded bore in nut 550. The distal end of the firing control wire 490 extends into a retainer pusher 554 set in a retainer pusher sleeve 556, both of which are shown in FIG. 14E and which is described in more detail in US. Publication No. 2005/0277954. In general, rotation of the firing knob 430 is effective to rotate the firing control wire 490. Since the firing control wire 490 is threadably mated to the nut 550, which is fixed between the proximal and distal portions of the elongate shaft 452, the threaded bore in nut 550 will cause the firing control wire 490 to move distally through the elongate shaft 452, thereby advancing the retainer pusher 554 in a distal direction. The retainer pusher 554 is positioned proximal to one or more retainers 500 stored within a garage 532 in the distal portion of the elongate shaft 452, and thus distal movement of the pusher 554 will advance the retainers 550 through the shaft 452 to position the distal most retainer within the jaws 524a and 524b of the end effector 520. A person skilled in the art will appreciate that a variety of other techniques can be used to advance a plurality of retainers through the elongate shaft and to position a retainer within the jaws.

Figure 16A:
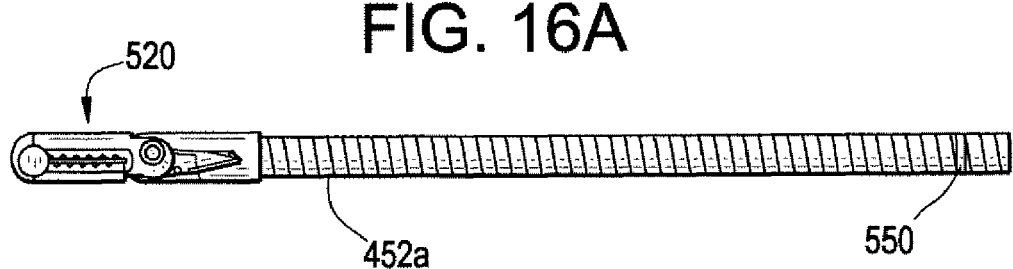
FIGS. 16A-16D are elevational views of the distal end of various embodiments of a plication device in accordance with the present invention.
Figure 16B:
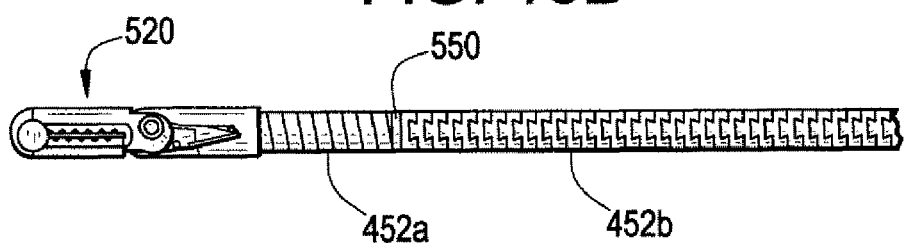
Figure 16C:
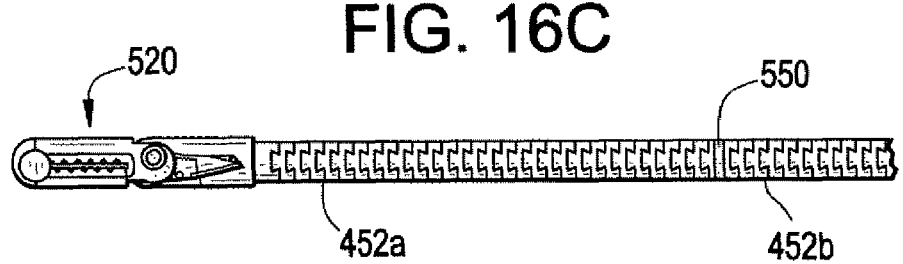
Figure 16D:
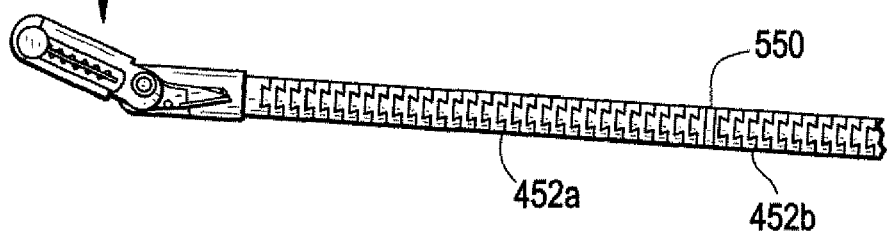

At the proximal end of the elongate shaft 452 is the coil connector 512 which is made of a metal, preferably brass, and is used as a means for connecting the proximal portion 452a of elongate shaft 452 to the handle assembly. Dual lumen inner sheath 560 has lumens for end-effector control wire 510 and firing control wire 490. Filler tube connector 562 is used to connect the coil connector 512 to the elongate shaft 452 and is glued to coil connector 512 and elongate shaft 452 using an adhesive glue such as cyanoacrylate. Elongate shaft 452 is broken into proximal shaft section 452a and distal shaft section 452b. Proximal shaft section 452a is preferably nitinol and has a dovetail laser pattern. Distal shaft section 452b is preferably stainless steel and has a similar dovetail pattern cut through the wall of the shaft. Other patterns could also be used such as a helical cut as shown in FIG. 16A. FIG. 16B depicts another variation of the plication device where the proximal shaft section is similar to that above but the nut is placed significantly more distally and the stainless steel distal shaft section with a dovetail pattern is replaced with a helical cut creating a ribbon coil. FIG. 16C depicts the placement of the nut and the dovetail patterns of the proximal and distal shaft portions discussed with respect to FIGS. 14A-F above. FIG. 16D depicts the passively articulating jaws of the alternative embodiment discussed above.

A preferred retainer 500 for us in the present system and method is shown in FIG. 15. Retainer 500 is comprised of stainless steel or other biocompatible material such as MP35N, platinum, nitinol and cobalt chromium or alloys thereof. The helical retainer may also be made of a or polymeric material such as one made of poly lactic acid (PLA) and/or poly glycolic acid (PGA). The retainer is comprised of a metal alloy with the preferred embodiment containing at least a trace of an element having an atomic number greater than 53 such as platinum to enhance visibility of the retainer under fluoroscopy. Additionally, a sufficient wall thickness should be chosen to ensure visibility under fluoro. The shape of the tip of the distal jaws of the plication device also have an alignment feature when viewed under fluoro that allows the viewer to determine which of 2 orientations (0/180 or 90/270) the jaws are in. In a 0/180 orientation the tip of the jaws form a circle as depicted in FIG. 14F. In a 90/270 orientation the tip of the jaws form a minus as depicted in FIG. 14B. The retainer 500 is preferably "C" shaped with elongated legs which may vary in length depending on the depth of tissue to be penetrated and the number of retainers that are desired to be housed within the garage of the plication device. The tips 501 are designed to be folded by the distal tips of the jaws of the end effector during the process of advancement to prevent the retainer from backing out or being pulled out of the plicated tissue. The retainer could be coated with one or more pharmacologically active agents such as heparin for the purpose of reducing thrombotic potential.

The plication device may further comprise a magnetic based location sensor such as those manufactured by Biosense Webster for sensing the location and orientation (six degrees of freedom, x, y, z, roll (Xrot), pitch (Yrot) and yaw (Zrot)) of the distal end of the deflecting guide catheter and for providing location information that may be registered with other preaquired or real-time images or otherwise used to depict the location of the distal end of the deflecting guide catheter on a real-time display map of the heart. Systems such as the Carto® system produced by Biosense Webster would be useful for this purpose. The incorporation of the magnetic based location sensor near the distal tip of the plication device, preferably approximately 28 mm proximal from the distal tip, enables precise orientation of the jaws in order to facilitate placement of the jaws and plication of the tissue. The magnetic location sensors would be placed proximal the distal end of the jaws of the plication device due to shielding if such sensors were placed in the jaws themselves. Location information is then transmitted through electrical conductors to circuitry in the handle of the plication device which is electrically connected to a Carto® mapping system. The Carto® mapping system will then use the location information from the magnetic location sensors in order to extrapolate the location and layout of the distal end of the plication device. A sensor should also be placed in the handle of the plication device that would provide a signal to the Carto® system indicative of the open/closed position of the jaws. With this information the Carto® system will be able to display a real-time image of the heart and the location of the distal end of the plication device within the left ventricle, etc.

The devices disclosed herein can also be designed to be disposed of after a single use, or they can be designed to be used multiple times. In either case, however, the device can be reconditioned for reuse after at least one use. Reconditioning can include any combination of the steps of disassembly of the device, followed by cleaning or replacement of particular pieces, and subsequent reassembly. In particular, the device can be disassembled, and any number of the particular pieces or parts of the device can be selectively replaced or removed in any combination. Upon cleaning and/or replacement of particular parts, the device can be reassembled for subsequent use either at a reconditioning facility, or by a surgical team immediately prior to a surgical procedure. Those skilled in the art will appreciate that reconditioning of a device can utilize a variety of techniques for disassembly, cleaning and/or replacement, and reassembly. Use of such techniques, and the resulting reconditioned device, are all within the scope of the present application.

The preceding description has been presented with reference to presently preferred embodiments of the invention. Workers skilled in the art and technology to which this invention pertains will appreciate that alterations and changes in the described structure may be practiced without meaningfully departing from the principal, spirit and scope of this invention.

Accordingly, the foregoing description should not be read as pertaining only to the precise structures described and illustrated in the accompanying drawings, but rather should be read consistent with and as support to the following claims which are to have their fullest and fair scope.

What is claimed is:

1. A method for the percutaneous treatment of mitral valve regurgitation by reshaping a mitral valve annulus through an arterial access site in a patient comprising the steps of:
    inserting a crossing catheter and a deflecting guide catheter having a lumen therethrough ending in a distal opening into the arterial access site of the patient;
    advancing the crossing catheter through the aortic valve into the left ventricle;
    advancing the deflecting guide catheter over the crossing catheter through the aortic valve into the left ventricle;
    withdrawing the crossing catheter from the patient;
    positioning the deflectable guide catheter with the distal opening pointing towards the underside of the mitral valve annulus;
    introducing a plication device into the arterial access site through the lumen of the deflectable guide catheter and advancing the plication device out the distal opening of the deflectable guide catheter within the left ventricle, the plication device comprising a pair of opposing jaws operable to plicate tissue;
    positioning the plication device at a first position on the underside of the mitral valve at or near the annulus;
    plicating a first portion of tissue of the mitral valve using the plication device to create a first tissue plication; and;
    applying a retainer to the first tissue plication.

2. The method of claim 1 further comprising the step of:
    examining the first tissue plication using an imaging method to produce an image of the mitral valve; and,
    determining if the plication is acceptable prior to the step of applying the retainer.

3. The method of claim 2 further comprising the step of:
    releasing the plication if the plication is determined not to be appropriate at the examining step;
    repositioning the plication device at a second position in the subvalvular groove of the mitral valve annulus; and,
    plicating a first portion of tissue of the mitral valve at or near the annulus using the plication device to create a first tissue plication.

4. The method of claim 2 wherein the imaging method is fluoroscopy.

5. The method of claim 4 wherein the plication device comprises a distal tip that forms a first shape when viewed in a first orientation and forms a second shape when viewed in a perpendicular orientation.

6. The method of claim 4 further comprising the step of registering pre-acquired CT or MRI image data with the fluoroscopic image.

7. The method of claim 4 further comprising the step of acquiring a three-dimensional real-time ultrasound image and registering such image with the fluoroscopic image.

8. The method of claim 2 wherein the imaging method creates a three-dimensional profile of the plication device by using x-ray images acquired in at least two planar projections in real-time.

9. The method of claim 2 wherein the imaging method is rotational angiographic imaging.

10. The method of claim 2 wherein the imaging method is intracardiac echography (ICE) thereby producing an ICE image.

11. The method of claim 10 wherein the ICE image is produced by an ICE catheter placed inside one of the chambers of the heart.

12. The method of claim 11 wherein the chamber is the right ventricle.

13. The method of claim 11 wherein the chamber if the right atrium.

14. The method of claim 10 wherein the ICE image is produced by an ICE catheter placed inside one of the great vessels of the patient.

15. The method of claim 2 wherein the imaging method is transeophagael echo (TEE).

16. The method of claim 2 further comprising the step of determining whether the plication achieves the desired impact on the function of the mitral valve prior to applying the retainer to the plication.

17. The method of claim 16 wherein the step of determining whether the desired impact has been achieved is performed using color Doppler ultrasound imaging.

18. The method of claim 17 wherein an ultrasound contrast agent is administered to the patient.

19. The method of claim 16 wherein the step of determining whether the desired impact has been achieved is performed using an x-ray contrast bolus injection into one of the chambers of the heart.

20. The method of claim 19 wherein the chamber of the heart is the left ventricle.

21. The method of claim 16 wherein the imaging method is bi-planar angiographic imaging.

22. The method of claim 16 wherein the imaging method is intra-chamber optical imaging.

23. The method of claim 22 wherein the deflectable guide catheter comprises an optical imaging system.

24. The method of claim 23 wherein the optical imaging system uses infrared wavelengths.

25. The method of claim 16 wherein the step of determining whether the desired impact has been achieved is based on the presence and degree of mitral valve regurgitation.

26. The method of claim 2 wherein the method of imaging utilizes x-rays.

27. The method of claim 2 further comprising the step of determining a location for the first tissue plication based on an optimization plan generated using a three-dimensional functional numerical simulation based on imaging data generated by the imaging method.

28. The method of claim 27 wherein the generation of the optimization plan is performed prior to step of inserting the crossing catheter.

29. The method of claim 27 wherein the generation of the optimization plan is performed after the step of applying a retainer to the first tissue plication.

30. The method of claim 1 further comprising the steps of:
determining if the first tissue plication as retained by the retainer sufficiently reshapes the mitral valve annulus to treat the mitral valve regurgitation;
repositioning the deflectable guide catheter to a second position on the underside of the mitral valve at or near the annulus;
introducing a second plication device or using a reloaded multi-retainer plication device in the delivery guide catheter and positioning the second plication device in the subvalvular region of the mitral valve;
plicating a second portion of tissue of the mitral valve at or near the annulus using the plication device to create a second tissue plication; and;
applying a retainer to the second tissue plication.

31. The method of claim 30 further comprising the steps of:
withdrawing the deflectable guide catheter and the plication device;
closing the arterial access site.

32. The method of claim 30 further comprising the step of determining whether the first plication with a retainer achieves the final desired impact on the function of the mitral valve prior to introducing a second plication device into the deflecting guide catheter.

33. The method of claim 1 wherein the retainer is comprised of a metal alloy.

34. The method of claim 33 wherein the retainer is comprised of stainless steel, MP35N, platinum, nitinol, cobalt chromium or alloys thereof.

35. The method of claim 34 wherein the retainer is comprised of an alloy containing at least a trace of an element having an atomic number greater than 53 to enhance visibility of the retainer under fluoroscopy.

36. The method of claim 1 wherein the retainer is comprised of poly lactic acid (PLA) and/or poly glycolic acid (PGA).

37. The method of claim 1 wherein the deflecting guide catheter comprises at least one location sensor for sensing the location of the distal end of the deflecting guide catheter in three dimensions in real-time.

38. The method of claim 37 wherein a profile of the deflecting guide catheter is constructed based on location information in three-dimensional space and information regarding the pitch, roll and yaw of the distal end of the deflecting guide from the at least one location sensor.

39. A method for the percutaneous treatment of mitral valve regurgitation by reshaping a mitral valve annulus through a venous access site in a patient comprising the steps of:
accessing the right atrium through the venous access site with a transseptal access catheter;
puncturing the septum using the transseptal access catheter
advancing a deflecting guide catheter over the transseptal access catheter through the septal puncture into the left atrium;
withdrawing the transseptal access catheter from the patient;
positioning the deflectable guide catheter with the distal opening pointing towards the mitral valve annulus;
introducing a plication device into the venous access site through the lumen of the deflectable guide catheter and advancing the plication device out the distal opening of the deflectable guide catheter, the plication device comprising a pair of opposing jaws operable to plicate tissue;
positioning the plication device at a first position on the atrial side of the mitral valve at or near the annulus;
plicating a first portion of tissue of the mitral valve using the plication device to create a first tissue plication; and;
applying a retainer to the first tissue plication.

40. The method of claim 39 further comprising the step of:
examining the first tissue plication using an imaging method to produce an image of the mitral valve; and,
determining if the plication is acceptable prior to the step of applying the retainer.

41. The method of claim 40 further comprising the step of:
releasing the plication if the plication is determined not to be appropriate at the examining step;
repositioning the plication device at a second position at or near the mitral valve annulus; and,
plicating a first portion of tissue of the mitral valve at or near the annulus using the plication device to create a first tissue plication.

42. The method of claim 40 further comprising the steps of:
determining if the first tissue plication as retained by the retainer sufficiently reshapes the mitral valve annulus to treat the mitral valve regurgitation;
repositioning the deflectable guide catheter to a second position at or near the annulus of the mitral valve;
introducing a second plication device or using a reloaded multi-retainer plication device in the delivery guide catheter and positioning the second or reloaded plication device at or near the annulus of the mitral valve;
plicating a second portion of tissue of the mitral valve at or near the annulus using the plication device to create a second tissue plication; and;
applying a retainer to the second tissue plication.

43. The method of claim 42 further comprising the steps of:
withdrawing the deflectable guide catheter and the plication device;
closing the venous access site.

* * * * *